US008021644B2

(12) United States Patent
Hellerstein (10) Patent No.: US 8,021,644 B2
(45) Date of Patent: Sep. 20, 2011

(54) METHODS FOR MEASURING RATES OF REVERSE CHOLESTEROL TRANSPORT IN VIVO, AS AN INDEX OF ANTI-ATHEROGENESIS (75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 332 days.

(21) Appl. No.: 11/888,976

(22) Filed: Aug. 3, 2007

(65) Prior Publication Data
US 2008/0003179 A1 Jan. 3, 2008

Related U.S. Application Data (62) Division of application No. 10/519,121, filed as application No. PCT/US03/29361 on Sep. 15, 2003, now Pat. No. 7,255,850.

(60) Provisional application No. 60/410,352, filed on Sep. 13, 2002.

(51) Int. Cl.
A61K 51/00 (2006.01)
(52) U.S. Cl. ...................................... 424/1.45
(58) Field of Classification Search ................... 424/1.45
See application file for complete search history.

(56) References Cited

U.S. PATENT DOCUMENTS

| 4,065,552 | A | 12/1977 | Costa |
| 4,332,784 | A | 6/1982 | Smith et al. |
| 4,889,126 | A | 12/1989 | Doddrell et al. |
| 4,940,658 | A | 7/1990 | Allen et al. |
| 5,026,909 | A | 6/1991 | Zoltarev et al. |
| 5,042,488 | A | 8/1991 | Ackerman |
| 5,167,948 | A | 12/1992 | Wenzel |
| 5,209,919 | A | 5/1993 | Turteltaub et al. |
| 5,317,098 | A | 5/1994 | Shizuya et al. |
| 5,338,686 | A | 8/1994 | Hellerstein |
| 5,354,662 | A | 10/1994 | Stone et al. |
| 5,376,355 | A | 12/1994 | Turteltaub et al. |
| 5,394,236 | A | 2/1995 | Murnick |
| 5,439,803 | A | 8/1995 | Ross et al. |
| 5,506,147 | A | 4/1996 | Kolhouse et al. |
| 5,597,548 | A | 1/1997 | Sherry et al. |
| 5,665,377 | A | 9/1997 | Gonella |
| 5,665,562 | A | 9/1997 | Cook |
| 5,783,445 | A | 7/1998 | Murnick |
| 5,855,921 | A | 1/1999 | Somlyai |
| 5,910,403 | A | 6/1999 | Hellerstein |
| 5,916,537 | A | 6/1999 | Kajiwara et al. |
| 5,922,554 | A | 7/1999 | Fielding et al. |
| 5,924,995 | A | 7/1999 | Klein et al. |
| 5,961,470 | A | 10/1999 | Wagner et al. |
| 6,010,846 | A | 1/2000 | Hellerstein |
| 6,031,228 | A | 2/2000 | Abramson |
| 6,071,245 | A | 6/2000 | Kohno et al. |
| 6,117,656 | A | 9/2000 | Seed |
| 6,284,219 | B1 | 9/2001 | Ajami |
| 6,329,208 | B1 | 12/2001 | Jones et al. |
| 6,355,416 | B1 | 3/2002 | Abramson |
| 6,461,806 | B1 | 10/2002 | Hellerstein |
| 6,461,870 | B2 | 10/2002 | Yatscoff et al. |
| 6,468,802 | B1 | 10/2002 | Yatscoff et al. |
| 6,599,750 | B2 | 7/2003 | Yatscoff et al. |
| 6,602,715 | B2 | 8/2003 | Yatscoff et al. |
| 6,610,270 | B1 | 8/2003 | Ajami |
| 6,625,547 | B1 | 9/2003 | Korzekwa et al. |
| 6,642,059 | B2 | 11/2003 | Chait et al. |
| 6,653,076 | B1 | 11/2003 | Franza, Jr. et al. |
| 6,653,090 | B1 | 11/2003 | Lopaschuk |
| 7,449,171 | B2 | 12/2003 | Hellerstein |
| 6,680,203 | B2 | 1/2004 | Dasseux et al. |
| 6,764,817 | B1 | 7/2004 | Schneider |
| 6,783,751 | B2 | 8/2004 | Heumann |
| 6,808,875 | B2 | 10/2004 | Hellerstein |
| 6,835,927 | B2 | 12/2004 | Becker et al. |
| 6,849,396 | B2 | 2/2005 | Schneider |
| 6,872,575 | B2 | 3/2005 | Regnier |
| 6,887,712 | B1 | 5/2005 | Medford et al. |
| 6,902,719 | B2 | 6/2005 | Wagner |
| 6,906,320 | B2 | 6/2005 | Sachs et al. |
| 7,001,587 | B2 | 2/2006 | Hellerstein |
| 7,022,834 | B2 | 4/2006 | Hellerstein |
| 7,048,907 | B2 | 5/2006 | Groman et al. |
| 7,057,168 | B2 | 6/2006 | Miller et al. |
| 7,084,396 | B2 | 8/2006 | Schneider |

(Continued)

FOREIGN PATENT DOCUMENTS

EP 0826377 A1 3/1998

(Continued)

OTHER PUBLICATIONS

Aydemir et al. "Effects of defibrotide on aorta and brain melondialdehyde and antioxidants in cholesterol-induced atherosclerotic raggits", Int J Clin Lab Res 2000, 30:101-107.*
"New Diagnostic Technique Could Help Treat AIDS," Agence France-Presse, Dow Jones News/Retrieval, Feb. 17, 1998, pp. 1-2.
Adami, H.O. et al. (1995). "The Aetiology and Pathogenesis of Human Breast Cancer," *Mutation Research* 333:29-35.
Airhart, J. et al. (1974). "Compartmentation of Free Amino Acids for Protein Synthesis in Rat Liver," *Biochem J.* 140:539-545.
Ajie, H.O. et al. (1995). "In Vivo Study of the Biosynthesis of Long-Chain Fatty Acids Using Deuterated Water," *Am. J. Physiol.* 269:E247-E252.

(Continued)

*Primary Examiner* — Sue Liu
*Assistant Examiner* — Bin Shen
(74) *Attorney, Agent, or Firm* — Morrison & Foerster LLP (57) ABSTRACT

The present invention relates to biochemical methods for determining reverse cholesterol transport. Specifically, the rates of the two arms of reverse cholesterol transport (HDL or first arm and post-HDL or second arm) are obtained by measuring the flow of unlabeled cholesterol from tissues into plasma HDL and from plasma HDL to bile acids.

4 Claims, 2 Drawing Sheets

U.S. PATENT DOCUMENTS

| | | | |
|---|---|---|---|
| 7,255,850 B2 | 8/2007 | Hellerstein |
| 7,256,047 B2 | 8/2007 | Malloy et al. |
| 7,262,020 B2 | 8/2007 | Hellerstein |
| 7,307,059 B2 | 12/2007 | Hellerstein |
| 7,504,233 B2 | 3/2009 | Hellerstein |
| 2003/0068634 A1 | 4/2003 | Hellerstein |
| 2003/0119069 A1 | 6/2003 | Schneider et al. |
| 2003/0133871 A1 | 7/2003 | Hellerstein |
| 2003/0148533 A1 | 8/2003 | Malloy et al. |
| 2003/0180710 A1 | 9/2003 | Lee et al. |
| 2003/0180800 A1 | 9/2003 | Lee et al. |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza et al. |
| 2005/0014181 A1 | 1/2005 | Galis et al. |
| 2005/0092910 A1 | 5/2005 | Geromanos et al. |
| 2005/0118724 A1 | 6/2005 | Bateman et al. |
| 2005/0153346 A1 | 7/2005 | Schneider |
| 2005/0175982 A1 | 8/2005 | Iwatani et al. |
| 2005/0201937 A1 | 9/2005 | Hellerstein |
| 2005/0202406 A1 | 9/2005 | Hellerstein |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0020440 A1 | 1/2006 | Hellerstein |
| 2006/0029549 A1 | 2/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider |
| 2006/0204439 A1 | 9/2006 | Hellerstein |
| 2006/0251576 A1 | 11/2006 | Hellerstein |
| 2006/0280682 A1 | 12/2006 | Hellerstein |
| 2007/0248540 A1 | 10/2007 | Hellerstein |
| 2008/0003179 A1 | 1/2008 | Hellerstein |
| 2009/0041661 A1 | 2/2009 | Hellerstein |

FOREIGN PATENT DOCUMENTS

| | | | |
|---|---|---|---|
| JP | 2001-211782 A | 8/2001 |
| SU | 968036 | 10/1982 |
| WO | WO-90/11371 A1 | 10/1990 |
| WO | WO-93/20800 A1 | 10/1993 |
| WO | WO-93/25705 A1 | 12/1993 |
| WO | WO-95/13096 A1 | 5/1995 |
| WO | WO-98/51820 A1 | 11/1998 |
| WO | 2000/012535 A2 | 3/2000 |
| WO | WO-00/13025 A1 | 3/2000 |
| WO | WO-00/63683 A1 | 10/2000 |
| WO | WO-01/80715 | 11/2001 |
| WO | WO-01/84143 A1 | 11/2001 |
| WO | WO-03/061479 A1 | 7/2003 |
| WO | WO-03/068919 A2 | 8/2003 |
| WO | WO-03/087314 A2 | 10/2003 |
| WO | WO-2004/003493 A2 | 1/2004 |
| WO | WO-2004/011426 A2 | 2/2004 |
| WO | WO-2004/021863 A2 | 3/2004 |
| WO | WO-2004/024941 A2 | 3/2004 |
| WO | WO-2004/025270 A2 | 3/2004 |
| WO | WO-2004/042360 A2 | 5/2004 |
| WO | WO-2005/009597 A2 | 2/2005 |
| WO | WO-2005/015155 A2 | 2/2005 |
| WO | WO-2005/033652 A2 | 4/2005 |
| WO | WO-2006/050130 A3 | 5/2006 |
| WO | WO-2006/081521 A3 | 8/2006 |
| WO | WO-2006/107814 A2 | 10/2006 |

OTHER PUBLICATIONS

Anderson, R.W. et al. (1998). "Direct HIV Cytopathicity Cannot Account for CD4 Decline in AIDS in the Presence of Homeostasis: A Worst-Case Dynamic Analysis," *J. AIDS and Human Retrovirology* 17:245-252.

Antelo, Fernando et al. (2002). "Adipose Triglyceride (TG) Turnover and De Novo Lipogenesis (DNL) in Humans: Measurement by Long-Term 2H2O Labeling and Mass Isotopomer Distribution Analysis (MIDA)," *Experimental Biology*16 [Meeting Abstract 361.10]: A400.

Asher, E. et al. (1995). "Evaluation of Cell Death in EBV-Transformed Lymphocytes Using Agarose Gel Electrophoresis, Light Microscopy and Electron Microscopy," *Leukemia and Lymphoma* 19:107-119.

Attardi, Giuseppe et al. (1988). "Biogenesis of Mitochondria," *Ann. Rev. Cell Biol.* 4:289-333.

Australian Patent Office Search Report mailed Aug. 26, 2005, for Singapore patent application No. SG 200500571-5, filed Jul. 25, 2003, 5 pages.

Bach, Simon P. et al. (2000). "Stem Cells: The Intestinal Stem as a Paradigm," *Carcinogenesis* 21(3):469-476.

Bandsma, Robert H.J. et al. (1998). "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile," *Biochem. J.* 329:699-703.

Bandsma. Robert H.J. et al. (2000). "The Contribution of Newly Synthesized Cholesterol to Bile Salt Synthesis in Rats Quantified By Mass Isotopomer Distribution Analysis," *Biochemica et Biophysica Acta* 1483:343-351.

Bertani, Roberta et al. (Jan. 2002). "Measurement of Total Body Water (TBW) Through In Vivo Dilution of Tracer Compounds: Use of D2O and its Determination by FT Infrared Spectroscopy," *Annali diChimica* 92:135-138.

Bickenbach, J.R. (1981). "Identification and Behavior of Label-Retaining Cells in Oral Mucosa and Skin," *J Dent Res* pp. 1611-1620.

Bier, D. M. (Nov. 1987). "The Use of Stable Isotopes in Metabolic Investigation," *Balliere's Clinical Endocrinology and Metabolism* 1(4):817-836.

Bier, D.M. (1997). "Stable Isotopes in Biosciences, Their Measurement and Models for Amino Acid Metabolism," *Eur J Pediatr* 156 [Supp. 1]:S2-S8.

Bingham, S.A. (Jan. 1994)."The Use of 24-h Urine Samples and Energy Expenditure to Validate Dietary Assessments," *American Journal of Clinical Nutrition* 59 [1 Supp.]:227S-231S.

Black, G.E. et al. (Jan. 2001). "Labeling DNA with Stable Isotopes: Economical and Practical Considerations," *BioTechniques* 30:134-140.

Blair, Steven N. et al. (1995). "Changes in Physical Fitness and All-Cause Mortality: A Prospective Study of Healthy and Unhealthy Men," *JAMA* 273(14): 1093-1098.

Blau, K. and Halket, J. eds. (1993). *Handbook of Derivatives for Chromatography, 2nd Edition*. John Wiley & Sons Ltd., England.

Bonotto, S. et al. (1977). "Study of the Distribution and Biological Effects of 3H in the Algae Acetabularia, Chlamydomonas and Porphyra," *Current Topics in Radiation Quarterly* 12:115-132.

Bravo, Elena et al. (1994). "Decreased Hepatic Uptake and Processing of High Density Lipoprotein Unesterified Cholesterol and Cholesteryl Ester with Age in the Rat," *J. Biochem.* 116:1088-1095.

Brown, Alan S. et al (1998). "Treating Patients with Documented Atherosclerosis to National Cholesterol Education Program-Recommended Low-Density-Lipoprotein Cholesterol Goals with Atorvastatin, Fluvastatin, Lovastatin and Simvastatin," *J. Am. Coll. Cardiol.* 32:665-672.

Bucy, R.P. et al. (1998). "Analysis of Lymph Node Biopsies in HIV Infected Patients Before and After HAART," *Abstract, 5th Conference on Retroviruses and Opportunistic Infections, Session 66* 519:177.

Caldwell, K.A. et al. (1993). "Quantification of Peptide Isotopomer Abundances and Determination of Protein (sic) Turnover Rates by Using Mass Isotopomer Distribution Analysis," *Abstract, 41st Annual Amer. Society Mass Spectrometry on Mass Spectrometry*, p. 331a.

Cassella, C.R. et al. (1997). "Mechanisms of Lymphocyte Killing by HIV," *Current Opinion in Hematology* 4:24-31.

Cesar, D. et al. (1998). "Direct Measurement of CD4+ and CD8+ T Cell Proliferation Rates in Vivo in AIDS Patients Using a Stable Isotope-Mass Spectrometric Technique," *Abstract, 5th Conference on Retroviruses and Opportunistic Infections*, Chicago Illinois.

Chinkes, David L. et al. (1996). "Comparison of Mass Isotopomer Dilution Methods Used to Calculate VLDL Production in Vivo," *Am. J. Physiol.* 271 (*Endocrinol. Metab.* 34):E373-E383.

Christiansen Mark P. et al. (Oct. 2000). "Effect of Dietary Energy Restriction on Glucose Production and Substrate Utilization in Type 2 Diabetes," *Diabetes* 49:1691-1699.

Clayton, David (1991). "Replication and Transcription of Vertebrate Mitochondrial DNA," *Annu. Rev. Cell Biol.* 7:453-478.

Cohen, A. et al. (1983). "Purine and Pyrimidine Metabolism in Human T Lymphocytes," *J. Biol. Chem.* 258(20):12334-12340.

Cohen, J. (1998). "Failure Isn't What It Used to Be . . . But Neither is Success," *Science* 279:1133-1134.

Collins, Michelle L. et al. (Jan. 31, 2003). "Measurement of mitochondrial DNA synthesis in vivo using a stable isotope-mass spectrometric technique," *J Appl Physiol* 94:2203-2211.

Conners, M. et al. (1997). "HIV Infection Induces Changes in CD4+ T-Cell Phenotype and Depletions Within the CD4+ T-Cell Repertoire that are not Immediately Restored by Antiviral or Immune-Based Therapies," *Nature Medicine* 3(5):533-540.

Conrads, Thomas P. et al. (Jan. 2002). "Stable Isotope Labeling in Proteomics," *The Synthesis Cambridge Isotope Laboratories* 3(2):1-3.

Craig, Suzanne B. et al. (Sep. 1996). "The Impact of Physical Activity on Lipids, Lipoproteins, and Blood Pressure in Preadolescent Girls," *Pediatrics* 98 (3):389-395.

Crain, P.F.(1990). "Preparation and Enzymatic Hydrolysis of DNA and RNA for Mass Spectrometry," *Meth. Enz.*193:782-790.

Dalvie, D. (2000). "Recent Advances in the Application of Radioisotopes in Drug Metabolism, Toxicology and Pharmacokinetics," *Current Pharmaceutical Design* 6:1009-1028.

Davis, Ajuah et al. (Jul. 2000). "Effect of Pinitol Treatment on Insulin Action in Subjects With Insulin Resistance," *Diabetes Care* 23(7):1000-1005.

Deeks, S. et al. (1998). "Viral Load and CD4+ T Cell Changes in Patients Failing Potent Protease Inhibitor Therapy," *Abstract, 5th Conference on Retroviruses and Opportunistic Infections, Session 53* 419:158.

Deeks, Steven G. et al. (2002). "CD4+ T Cell Kinetics and Activation in Human Immunodeficiency Virus-Infected Patients Who Remain Viremic Despite Long-Term Treatment with Protease Inhibitor-Based Therapy," *Journal of Infectious Diseases* 185:315-323.

Dekker, Evelien et al. (1997). "Glucose Homeostasis in Children with *Falciparum malaria*: Precursor Supply Limits Gluconeogenesis and Glucose Production," *J Clin Endocrinol Metabol* 82:2514-2521.

Dimitrov, D.S. et al. (1995). "Scientific Correspondence," *Nature* 375:194-195.

Etnier, E.L. et al. (1984). "Metabolism of Organically Bound Tritium in Man," *Radiat. Res.* 100:487-502.

Fagerquist, Clifton K. et al. (1999). "Molecular Ion Fragmentation and Its Effects on Mass Isotopomer Abundance of Fatty Acid Methyl Estes Ionized by Electron Impact," *J Am Soc Mass Spectrom* 10:430-439.

Fagerquist, Clifton K. et al. (2001). "Elimination of the Concentration Dependence in Mass Isotopomer Abundance Mass Spectrometry of Methyl Palmitate Using Metastable Atom Bombardment," *J Am Soc Mass Spectrom* 12:754-761.

Gorochov, G. et al. (1998). "Perturbation of CD4+ and CD8+ T-Cell Repertoires During Progression to AIDS and Regulation of the CD4+ Repertoire During Antiviral Therapy," *Nature Medicine* 4(2):215-221.

Goz, Barry (1978). "The Effects of Incorporation of 5-Halogenated Deoxyuridines into DNA of Eukaryotic Cells," *Macological Reviews* 29(4):249-272.

Gratzner, H.G. (1982). "Monoclonal Antibody to 5-Broma-and 5-Iododeoxyuridine: A New Reagent for Detection of DNA Replication," *Science* 218:474-475.

Guo, Z.K. et al., (2000). "De novo lipogenesis in adipose tissue of lean and obese women: application of deuterated water and isotope ratio mass spectrometry," *International Journal of Obesity* 24:932-937.

Gygi, Steven et al. (2000). "Using Mass Spectrometry for Quantitative Proteomics," *Proteomics: A Trends Guide* pp. 31-36.

H Hellerstein, M. et al. (1997). "Measurement of Hepatic Ra UDP-glucose in Vivo in Rats: Relation to Glycogen Deposition and Labeling Patterns," *Am. J. Physiol.* 272:E155-E162.

Hansen, Andrew P. et al. (1992). "A Practical Method for Uniform Isotopic Labeling of Recombinant Proteins in Mammalian Cells," *Biochemistry* 31(51): 12713-12718.

Heck, Steven D. et al. (Apr. 1996). "Posttranslational amino acid epimerization: Enzyme-catalyzed isomerization of amino acid residues in peptide chains," *Proc. Natl. Acad. Sci.* USA 93(9):4036-4039.

Hellerstein, M. (1995). "Methods for Measurement of Fatty Acid and Cholesterol Metabolism," *Current Opinion in Lipidology* 6:172-181.

Hellerstein, M. (1999). "Measurement of T-Cell Kinetics: Recent Methodologic Advances," *Trends Immunology Today* 20(10):438-441.

Hellerstein, M. (1999). "The Changing Face of AIDS: Translators Needed," *Am J Clin Nutr* 70:787-788.

Hellerstein, M. (1999). "Mass Isotopomer Distribution Analysis at Eight Years: Theoretical, Analytic, and Experimental Considerations," *Am. J. Physiol.* 276:E1146-E1170.

Hellerstein, M. (2001). "No Common Energy: de Novo Lipogenesis as the Road Less Traveled," *Am J Clin Nutr* 74:707-708.

Hellerstein, M. (2002). "Carbohydrate-Induced Hypertriglyceridemia: Modifying Factors and Implications for Cardiovascular Risk," *Curr Opin Lipidol* 13:33-40.

Hellerstein, M. (2002). "Measurement of Synthesis Rates of Slow-turnover Proteins from 2H2O Incorporation into Non-essential Amino Acids (NEAA) and Application of Mass Isotopomer Distribution Analysis (MIDA)," *Faseb Journal Experimental Biology* 2002: Meeting Abstracts 16: A256.

Hellerstein, M. (2003). "In Vivo Measurement of Fluxes Through Metabolic Pathways: The Missing Link in Functional Genomics and Pharmaceutical Research," *Annu. Rev. Nutr.* 23:379-402.

Hellerstein, M. (2004). "New stable isotope-mass spectrometric techniques for measuring fluxes through intact metabolic pathways in mammalian systems: introduction of moving pictures into functional genomics and biochemical phenotyping," *Metabolic Engineering* 6:85-100.

Hellerstein, M. et al. (1986). "Glycoconjugates as Noninvasive Probes of Intrahepatic Metabolism: Pathways of Glucose Entry into Compartmentalized Hepatic UDP-glucose Pools during Glycogen Accumulation," *Proceedings of the National Academy of Sciences of the United States of America* 83(18):7044-7048.

Hellerstein, M. et al. (1992). "Mass Isotopomer Distribution Analysis: a Technique for Measuring Biosynthesis and Turnover of Polymers," *Am J Physiol* 263:E988-E1001.

Hellerstein, M. et al. (1993). "Model for Measuring Absolute Rates of Hepatic de Novo Lipogenesis and Reesterification of Free Fatty Acids," *Am. J. Physiol.* 265:E814-E820.

Hellerstein, M. et al. (1994). "Effects of Cigarette Smoking and its Cessation on Lipid Metabolism and Energy Expenditure in Heavy Smokers," *J. Clin. Invest.* 93:265-272.

Hellerstein, M. et al. (1994). "Mass Isotopomer Distribution Analysis for Measuring Fluxes Through Intracellular Metabolic Pathways and Biosynthetic Rates of Polymers," *IFAC Modeling and Control in Biomedical Systems*, pp. 353-359.

Hellerstein, M. et al. (1997). "Altered Fluxes Responsible For Reduced Hepatic Glucose Production and Gluconeogenesis by Exogenous Glucose in Rats," *Am. J. Physiol.* 272:E163-E172.

Hellerstein, M. et al. (1997). "Hepatic Gluconeogenic Fluxes and Glycogen Turnover During Fasting in Humans," *J. Clin. Invest.* 100(5):1305-1319.

Hellerstein, M. et al. (1997). "T Cell Turnover in HIV-1 Disease," *Immunity* 7:583-589.

Hellerstein, M. et al. (1999). "Directly Measured Kinetics of Circulating T Lymphocytes in Normal and HIV-1-Infected Humans," *Nature Medicine* 5(1):83-89.

Ho, D.D. et al. (1995). "Rapid Turnover of Plasma Virions and CD4 Lymphocytes in HIV-1 Infection," *Nature* 373:123-126.

Hoh, Rebecca et al. (1998). "De Novo Lipogenesis Predicts Short-Term Body-Composition Response by Bioelectrical Impedance Analysis to Oral Nutritional Supplements in HIV-Associated Wasting," *Am. J. Clin. Nutr.* 68:154-163.

Hsieh, Elaine A. et al. (2004). "Dynamics of Keratinocytes in Vivo Using 2H2O Labeling: A Sensitive Marker of Epidermal Proliferation State," *J Invest Dermatol* 123:530-536.

Hudgins, Lisa C. et al. (2000). "Relationship Between Carbohydrate-Induced Hypertriglyceridemia and Fatty Synthesis in Lean and Obese Subjects," *J. Lipid Res.* 41:595-604.

Hudgins, Lisa Cooper et al. (1996). "Human Fatty Acid Synthesis is Stimulated by a Eucaloric Low Fat, High Carbohydrate Diet," *J. Clin. Invest.* 97(9):2081-2091.

Hulzebos, C. V. et al. (2001). "Measurement of Parameters of Cholic Acid Kinetics in Plasma using a Microscale Stable Isotope Dilution Technique: Application to Rodents and Humans," *Journal of Lipid Research* 42:1923-1929.

Humphrey, Thomas J. et al. (1975). "A New Method for the Measurement of Protein Turnover," *Biochem. J.* 148:119-127.

Humphrey, Thomas J. et al. (1976). "A Sensitive Method for Measuring Protein Turnover Based on the Measurement of 2-3H-labeled Amino Acids in Proteins," *Biochem. J.* 156:561-568.

International Search Report mailed on Apr. 13, 2004, for PCT application No. PCT/US03/20052 filed on Jun. 25, 2003, 3 pages.

International Search Report mailed on Jun. 29, 2004, for PCT patent application No. PCT/US03/04183 filed on Feb. 12, 2003, 4 pages.

International Search Report mailed Jul. 8, 2004, for PCT patent application No. PCT/US03/27623 filed on Sep. 4, 2003, 4 pages.

International Search Report mailed on Jul. 9, 2004, for PCT patent application No. PCT/US03/35107 filed on Nov. 4, 2003, 2 pages.

International Search Report mailed Aug. 18, 2004, for PCT application PCT/US03/23340, filed Jul. 25, 2003, 2004: 4 pages.

International Search Report mailed on Aug. 18, 2004, for PCT application PCT/US03/29526, filed Sep. 16, 2003, 3 pages.

International Search Report mailed on Aug. 20, 2004, for PCT application No. PCT/US03/10554 filed on Apr. 4, 2003, 4 pages.

International Search Report mailed on Jan. 19, 2005, for PCT patent application No. PCT/US03/29361 filed on Sep. 15, 2003, 4 pages.

International Search Report mailed on Mar. 25, 2005, for PCT application No. PCT/US04/39722 filed on Nov. 24, 2004, 3 pages.

International Search Report mailed on Apr. 4, 2005, for PCT application No. PCT//US04/21063 filed on Jun. 29, 2004, 2 pages.

International Search Report mailed Aug. 1, 2005, for PCT application No. PCT/US2005/08265, filed Mar. 11, 2005, 4 pages.

International Search Report and Written Opinion mailed Oct. 11, 2007, for PCT Application No. PCT/US05/05660 filed Feb. 22, 2005, 11 pages.

James, J.S. (1998). "Clinical Implications of Virological Failure: Interview with Steven Deeks, M.D., San Francisco General Hospital," *AIDS Treatment News* 289:6-7.

Jennings, Graham et al. (Jul. 1999). "The Use of Infrared Spectrophotometry for Measuring Body Water Spaces," *Clinical Chemistry* 45(7):1077-1081.

Jones, J. G. (2001). "An Integrated $^2$H and $^{13}$C NMR Study of Gluconeogenesis and TCA Cycle Flux in Humans," *American Journal of Physiology-Endocrinology and Metabolism* 281:E848-856.

Jones, Peter J.H. et al. (1994). "Interaction of Dietary Fat Saturation and Cholesterol Level on Cholesterol Synthesis Measured Using Deuterium Incorporation," *Journal of Lipid Research* 35:1093-1101.

Jung, Hye Rim. et al. (1999). "Metabolic Adaptations to Dietary Fat Malabsorption in Chylomicron-Deficient Mice," *Biochem. J.* 343:473-478.

Jungas, Robert L. (1698). "Fatty Acid Synthesis in Adipose Tissue Incubated in Tritiated Water," *Biochemistry* 7(10):3708-3717.

Katz, J. et al. (1976). "Futile Cycles in the Metabolism of Glucose," *Curr Top Cell Regul* 10:237-89.

Kelleher, Joanne K. et al. (1992). "Model Equations for Condensation Biosynthesis Using Stable Isotopes and Radioisotopes," *Am. J. Physiol.* 262:E118-E125.

Khairallah, Edward A. et al. (1976). "Mortimore. Assessment of Protein Turnover in Perfused Rat Liver: Evidence for Amino Acid Compartmentation from Differential Labeling of Free and tRNA-bound Valine," *J Biol Chem* 251(5):1375-1384.

Kim, J. et al. (2000). "A New Stable Isotope-Mass Spectrometric (MS) Method to Measure Proliferation Rates of Colon Epithelial Cells," *Faseb Journal* 14(4): A718.

Lammert, Ole et al. (2000). "Effects of Isoenergetic Overfeeding of Either Carbohydrate or Fat in Young Men," *British Journal of Nutrition* 84:233-245.

Lee, Chong Do et al. (1999). "Cardiorespiratory Fitness, Body Composition, and All-Cause and Cardiovascular Disease Mortality in Men 1-3," *Am J Clin Nutr* 69:373-380.

Lefebvre, P. J. (Jan. 1979). "Naturally Labeled 13C-Glucose: A New Tool to Measure Oxidation Rates of Exogenous Glucose," *Diabetes* 28(Suppl. 1):63-65.

Leung, Gordon K. et al. (2000). "A Deficiency of Microsomal Triglyceride Transfer Protein Reduces Apolipoprotein B Secretion," *The Journal of Biological Chemistry* 275(11):7515-7520.

Lewanczuk, Richard Z. et al. (2004). "Comparison of the [13 C] Glucose Breath Test to the Hyperinsulinemic-Euglycemic Clamp When Determining Insulin Resistance," *Diabetes Care* 27(2):441-447.

Lipkin, M. (1987). "Proliferation and Differentiation of Normal and Diseased Gastrointestinal Cells," In *Physiology of the Gastrointestinal Tract*, L.R. Johnson ed., Raven Press, New York, pp. 255-284.

Lipkin, Martin et al. (1963). "Cell Proliferation Kinetics in the Gastrointestinal Tract of Man. I. Cell Renewal in Colon and Rectum," *Journal of Clinical Investigations* 42(6):767-776.

Lutton, C. et al. (1990). "Critical analysis of the Use of 14C-acetate for Measuring In Vivo Rat Cholesterol Synthesis," *Reprod Nutr Dev.* 30:71-84.

Macallan, Derek C. et al. (1998)."Measurement of Cell Proliferation by Labeling of DNA with Stable Isotope-Labeled Glucose: Studies in Vitro, in Animals, and in Humans," *Proc. Natl. Acad. Sci.* 95:708-713.

Maentausta, O. et al. (1979). "Radioimmunoassay of Conjugated Cholic Acid, Chenodeoxycholic Acid, and Deoxycholic Acid from Human Serum, with Use of 125I-Labeled Ligands," *Clin. Chem.* 25(2):264-268.

Margolick, J.B. et al. (1995). "Failure of T-cell Homeostasis Preceding AIDS in HIV-1 Infection," *Nature Medicine* 1(7):674-680.

Maric, D. et al. (2000). "Functional Ionotropic Glutamate Receptors Emerge During Terminal Cell Division and Early Neuronal Differentiation of Rat Neuroepithelial Cells," *Journal of Neuroscience Research* 61(6):652-662.

Marin, S. et al. (2004). "Dynamic Profiling of the Glucose Metabolic Network in Fasted Rat Hepatocytes using [1,2-$^{13}$C$_2$]Glucose," *Biochemical Journal* 381:287-294.

Mathur-De Vré, R. et al. (1984). "Molecular Aspects of Tritiated Water and Natural Water in Radiation Biology," *Prog. Biophys. Molec. Biol.* 43:161-193.

McCloskey, J.A. (1990). "ElectronIonization Mass Spectra of Trimethylsilyl Derivatives of Nucleosides," *Meth. Enz.* 193:825-841.

McCune, J.M. (1997)."Thymic Function in HIV-1 Disease," *Seminars in Immunology* 9:397-404.

McCune, Joseph M. et al. (2000). "Factors Influencing T-Cell Turnover in HIV-1-Seropositive Patients," *J. Clin. Invest.* 105:R1-R8.

McLean, A.R. et al. (1995). "In Vivo Estimates of Division and Death Rates of Human T Lymphocytes," *Proc. Natl. Acad. Sci USA* 92:3707-3711.

Meier, P.R. et al. (Mar. 1981). "Rates of Protein Synthesis and Turnover in Fetal Life," *Am J Physiol.* 240(3):E320-E324.

Mellors, J.W. et al. (1995). "Quantitation of HIV-1 RNA in Plasma Predicts Outcome after Seroconversion," *Ann. Intern. Med.* 122:573-579.

Mellors, J.W. et al. (1996). "Prognosis in HIV-1 Infection Predicted by the Quantity of Virus in Plasma," *Science* 272:1167-70.

Messmer, Bradley T. et al. (Feb. 10, 2005). "In Vivo Measurements Document the Dynamic Cellular Kinetics of Chronic Lymphocytic Leukemia B Cells," *J. Clin. Invest.* doi:10.1172/JCI200523409.

Mewissen, D.J. et al. (1977). "Comparative Incorporation of Tritium from Tritiated Water Versus Tritiated Thymidine, Uridine or Leucine," *Curr Top Rad Res Quart* 12:225-254.

Michie, C.A. et al. (1992). "Lifespan of Human Lymphocyte Subsets Defined by CD45 Isoforms," *Nature* 360:264-265.

Misell, L. et al. (2000). "A new in Vivo Stable Isotope Method for Measuring Mammary Epithelial Cell Proliferation," *Faseb Journal Experimental Biology 2000* 14(4), Meeting Abstract 550.5:A786.

Mohri, Hiroshi et al. (2001). "Increased Turnover of T Lymphocytes in HIV-1 Infection and its Reduction by Antiretroviral Therapy," *J. Exp. Med.* 194(9):1277-1287.

Morris, Rebecca J. et al. (1997). "Evidence that a Slowly Cyling Subpopulation of Adult Murine Epidermal Cells Retains Carcinogen," *Cancer Research* 46:3061-3066.

Morris, Rebecca J. et al. (1997)."Evidence that Cutaneous Carcinogen-initiated Epithelial Cells from Mice are Quiescent Rather than Actively Cyling," *Cancer Research* 57:3436-3443.

Morsches, Bernhard (1976). "Tierexperimentelle Untersuchungen uber die Beziehungen zwischen der Hydroxyprolinausscheidung im Urin and den Hydroxyprolinfraktionen im Serum," *Der Hautarzt* 27:234-242.

Mosier, D.E. (1995). "CD4.sup.+ Cell Turnover," *Nature* 375:193-194.

Murali-Krishna, K. et al. (1998). "Counting Antigen-Specific CD8 T Cells: A Reevaluation of Bystander Activation during Viral Infection," *Immunity* 8:177-187.

Nanjee, M. N. et al. (2001). "Intravenous apoA-I/lecithin Discs Increase Pre-Beta-HDL Concentration in Tissue Fluid and Stimulate Reverse Cholesterol Transport in Humans," *Journal of Lipid Research* 42:1586-1593.

Neese, R. A. et al. (1993). "Measurement of Endogenous Synthesis of Plasma Cholesterol in Rats and Humans Using MIDA," *Am. J. Physiol.* 264:E139-E147.

Neese, R. A. et al. (Nov. 2002). "Measurement in vivo of Proliferation Rates of Slow Turnover Cells by 2H2O Labeling of the Deoxyribose Moiety of DNA," *PNAS* 99(24):15345-15350.

Neese, Richard A. et al. (1995). "Gluconeogenesis and Intrahepatic Triose Phosphate Flux in Response to Fasting or Substrate Loads." *Journal of Biological Chemistry* 270(24):14452-14463.

Neese, Richard A. et al. (2001). "Advances in the Stable Isotope-Mass Spectrometric Measurement of DNA Synthesis and Cell Proliferation," *Analytical Biochemistry* 298(2):189-195.

Ong, Shao-En et al. (2002). "Stable Isotope Labeling by Amino Acids in Cell Culture, SILAC, as a Simple and Accurate Approach to Expression Proteomics," *Molecular and Cellular Proteomics* 1:376-386.

Ouguerram, K. et al. (Jan. 2002)."A New Labeling Approach Using Stable Isotopes to Study In Vivo Plasma Cholesterol Metabolism in Humans," *Metabolism* 51(1):5-11.

Oyaizu, N. et al. (1995)."Role of Apoptosis in HIV Disease Pathogenesis," *J. of Clinical Immunology* 15(5):217-231.

Palmer, L.D. et al. (1997). "Telomere Length, Telomerase Activity, and Replicative Potential in HIV Infection: Analysis of CD4+ and CD8+ T Cells from HIV-discordant Monozygotic Twins," *J. Experimental Medicine* 185(7):1381-1386.

Pantaleo, Giuseppe (1999). "Unraveling the Strands of HIV's Web," *Nature Medicine* 5(1):27-28.

Papageorgopoulos, C. et al.(1993). "Toward the Measurement of Protein Synthesis by Mass Isotopomer Distribution Analysis (MIDA):Resolution of Isotopomers in a [d.sub.3 ]-Leucine Enriched Synthetic Oligopeptide Using Electrospray/Quadrupole Mass Spectrometry (ESI/MS)," *Abstract, Federation of American Societies for Experimental Biology* 1022:A177.

Papageorgopoulos, Christina et al. (1999). "Measuring Protein Synthesis by Mass Isotopomer Distribution Analysis (MIDA)," *Analytical Biochemistry* 267: 1-16.

Park, S. S., et al. (1997). "Measurement of Small Intestinal Cell Turnover with [6,6, 2H2] Glucose," *Berkeley Scientific, Abstract* 1(2):41-43.

Parks, Elizabeth J. et al. (1999). "Effects of a Low-Fat, High-Carbohydrate Diet on VLDL-Triglyceride Assembly, Production, and Clearance," *J. Clin. Invest.* 104(8):1087-1096.

Parks, Elizabeth J. et al. (2000). "Carbohydrate-induced Hypertriacylglycerolemia: Historical Perspective and Review of Biological Mechanisms," *Am. J. Nutr.* 71:412-433.

Parks, Elizabeth J. et al. (2000). "Dependence of Plasma a-Tocopherol Flux on Very Low-Density Triglyceride Clearance in Humans," *Free Radical Biology & Medicine* 29(11):1151-1159.

Paša-Tolic, Ljiljana et al. (1999). "High Throughput Proteome-Wide Precision Measurements of Protein expression Using Mass Spectrometry," *J. Am. Chem. Soc.* 121:7949-7950.

Patterson, Bruce W. (1993). "Concentration Dependence of Methyl-Palmitate Isotope Ratios by Electron Impact Ionization Gas Chromatography/Mass Spectrometry," *Biol. Mass Spectrom.* 22:481-486.

Patterson, Bruce W. et al. (Aug. 1997). "Measurement of Very Low Stable Isotope Enrichments by Gas Chromatography/Mass Spectrometry: Application to Measurement of Muscle Protein Synthesis," *Metabolism* 46(8):943-948.

Patton, G.M. et al. (Jul. 1979). "Measurements of Fatty Acid Synthesis by Incorporation of Deuterium from Deuterated Water," *Biochemistry* 18(14):3186-3188.

Perelson, A.S. et al.(1996)."HIV-1 Dynamics in Vivo: Virion Clearance Rate, Infected Cell Life-Span, and Viral Generation Time," *Science* 271:1582-1586.

Perelson, A.S. et al.(1997). "Decay Characteristics of HIV-1-Infected Compartments During Combination Therapy," *Nature* 387:188-191.

Pozharisski, K.M. et al. (1980). "Study of Kinetics of Epithelial Cell Populations in Normal Tissues of the Rat's Intestines and in Carcinogenesis," *Exp. Path., Bd.* 18:387-406.

Previs, Stephen F. et al. (2001). "Estimation of Protein Turnover In Vivo Using D2O," *Diabetes Abstract Book, 61st Scientific Sessions* 50[Supplement 2]:A301.

Ravichandran, L.V. et al., (Jun. 1991). "In vivo labeling studies on the biosynthesis and degradation of collagen in experimental myocardial infarction," *Biochemistry Journal* 24(3):405-414.

Reichard, P. (1978). "From Deoxynucleotides to DNA Synthesis," *Federation Proceedings* 37(1):9-14.

Reichard, P. (1988). "Interactions Between Deoxyribonucleotide and DNA Synthesis," *Ann. Rev. Biochem.* 57:349-374.

Roberts, S.B. (1989). "Use of the Doubly Labeled Water Method for Measurement of Energy Expenditure, Total Body Water, Water Intake, and Metabolizable Energy Intake in Humans and Small Animals," *Can. J. Physiol. Pharmacol.* 67(10):1190-1198.

Robin, Eugene D. et al. (1988). "Mitochondria DNA Molecules and Virtual Number of Mitochondria per Cell in Mammalian Cells," *Journal of Cellular Physiology* 136:507-513.

Rocha, B. et al. (1990). "Accumulation of Bromodeoxyuridine-Labelled Cells in Central and Peripheral Lymphoid Organs: Minimal Estimates of Production and Turnover Rates of Mature Lymphocytes," *Eur. J. Immunol.* 20:1697-1708.

Roda, Aldo et al. (1980). "Results with Six 'Kit' Radioimmunoassays for Primary Bile Acids in Human Serum Intercompared," *Clin. Chem.* 26(12) :1677-1682.

Roederer M. (Jul. 1995). "T-Dell Dynamics of Immunodeficiency," *Nature Medicine* 1(7):621-622.

Rooyackers, Olav E. et al. (Oct. 1996). "Tracer Kinetics Are of Limited Value to Measure in Vivo Protein Synthesis and Degradation Rates in Muscle of Anesthetized Rats," *Metabolism* 45(10):1279-1283.

Royale, G. T. et al. (1981). "Techniques for Investigating Substrate Metabolism in Patients," *Annals of the Royal College of Surgeons of England* 63:415-419.

Sawada, S. et al. (1995). "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver," *Mutation Research* 344:109-116.

Scalise, K. (Feb. 11-17, 1998). "Tracking T-Cells in AIDS Patients: A Safe Reliable Method of Measuring Human Cell Generation Rates," *Berkeleyan* p. 3.

Scheibner, Jurgen et al. (1993). "Bile Acid Synthesis from Newly Synthesized Vs. Preformed Cholesterol Precursor Pools in the Rat," *Hepatology* 17:1095-1102.

Scheibner, Jurgen et al. (1999). "Complex Feedback Regulation of Bile Acid Synthesis in the Hamster: The Role of Newly Synthsized Cholesterol," *Hepatology* 30:230-237.

Schneiter, P. et al. (1998). "Kinetics of Dexamethasone Induced Alterations of Glucose Metabolism in Healthy Humans," *American Journal of Physiology* pp. E806-E813.

Schwarz, Jean-Marc et al. (1995). "Short-Term Alterations in Carbohydrate Energy Intake in Humans," *J. Clin. Invest.* 96:2735-2743.

Shevchenko, Andrej et al. (1997). "Rapid 'de Novo' Peptide Sequencing by a Combination of Nanoelectrospray, Isotopic Labeling and a Quadrupole/Time-of-flight Mass Spectrometer," *Rapid Commun. Mass Spectrom.* 11:1015-1024.

Shigenaga, M.K. et al. (1994). "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection," *Methods in Enzymology* 234:16-33.

Siler, Scott Q. et al. (1998). "VLDL-Triglyceride Production After Alcohol Ingestion, Studied Using [2-13C1] Glycerol," *J. Lipid Res.* 39:2319-2328.

Siler, Scott Q. et al. (1998)."The Inhibition of Gluconeogenesis Following Alcohol in Humans," *Am. J. Physiol.* 275:E897-E907.

Smith, et al. (1983). "The Phosphogluconate Odixative Pathway," in *Principles of Biochemistry, 7th edition*, McGraw-Hill Book Company, pp. 417-423.

Sprent, J. et al. (1995). "CD4+ Cell Turnover," *Nature* 375:194.

Sunter, J.P. et al. (1978). "Cell Population Kinetics in the Epithelium of the Colon of the Male Rat," *Virchows Archiv. B Cell Path.* 26:275-287.

Supplementary Partial European Search Report mailed Aug. 17, 2005, for European patent application No. EP 03749756.7, filed Sep. 15, 2003, 6 pages.

Supplementary Partial European Search Report mailed Mar. 9, 2006, for European patent application No. EP 03713429.3, filed Feb. 12, 2003, 6 pages.

Supplementary Partial European Search Report mailed Sep. 22, 2006, for European patent application No. EP 03768624.3, filed Nov. 4, 2003, 4 pages.

Teixeira, Luciléia et al. (2001). "Poor CD4 T Cell Restoration After Supression of HIV-1 Replication May Reflect Lower Thymic Function," *AIDS* 15(14):1749-1756.

Tint, G.S. et al. (1974). "Transformation of 5α-cholest-7-en-3β-ol to Cholesterol and Cholestanol in Cerebrotendinous Xanthomatosis," *Journal of Lipid Research* 15:256-262.

Traber, P.G. et al. (1991). "Isolation of Intestinal Epithelial Cells for the Study of Differential Gene Expression Along the Crypt-Villus Axis," *Am. J. Physiol.* 260:G895-G903.

Trappe, T. A. et al. (2002). "Effect of Ibuprofen and Acetaminophen on Postexercise Muscle Protein Synthesis," *Am J Physiol Endocronol Metab* 282: E551-E556.

Turner, S. M. (2006). "Stable Isotopes, Mass Spectrometry, and Molecular Fluxes: Applications to Toxicology," *Journal of Pharmacological and Toxicological Methods* 53:75-85.

Turner, S. M. et al. (2005). "Emerging Applications of Kinetic Biomarkers in Preclinical and Clinical Drug Development," *Current Opinion in Drug Discovery & Development* 8(1):115-126.

Turner, Scott M. et al. (2002). "Measurement of Triglyceride (TG) Synthesis in Vivo 2H2O Incorporation into TG-Glycerol and Application of Mass Isotopomer Distribution Analysis (MIDA)," *Experimental Biology 2002* 16[Meeting Abstract 361.9]:A400.

U.S. Office Action mailed on Jun. 20, 2005, for U.S. Appl. No. 10/872,280, filed Jun. 17, 2004, 9 pages.

U.S. Office Action mailed on Oct. 18, 2005, for U.S. Appl. No. 10/366,125, filed Feb. 12, 2003, 29 pages.

U.S. Office Action mailed on Oct. 20, 2005, for U.S. Appl. No. 10/664,513, filed Sep. 16, 2003, 12 pages.

U.S. Office Action mailed on Mar. 30, 2006, for U.S. Appl. No. 10/664,513, filed Sep. 16, 2003, 15 pages.

U.S. Office Action mailed on Jun. 9, 2006, for U.S. Appl. No. 10/872,280, filed Jun. 17, 2004, 6 pages.

U.S. Office Action mailed on Jun. 26, 2006, for U.S. Appl. No. 10/366,125, filed Feb. 12, 2003, 11 pages.

U.S. Office Action mailed on Jul. 21, 2006, for U.S. Appl. No. 10/963,967, filed Oct. 12, 2004, 7 pages.

U.S. Office Action mailed on Aug. 8, 2006, for U.S. Appl. No. 10/519,121, filed Dec. 23, 2004, 8 pages.

U.S. Office Action mailed on Aug. 24, 2006, for U.S. Appl. No. 10/407,435, filed Apr. 4, 2003, 9 pages.

U.S. Office Action mailed on Jan. 11, 2007, for U.S. Appl. No. 10/963,967, filed Oct. 12, 2004, 6 pages.

U.S. Office Action mailed on Jan. 19, 2007, for U.S. Appl. No. 10,872,280, filed Jun. 17, 2004, 5 pages.

U.S. Office Action mailed on Jan. 24, 2007, for U.S. Appl. No. 10/701,990, filed Nov. 4, 2003, 6 pages.

U.S. Office Action mailed on Jan. 31,2007, for U.S. Appl. No. 11/078,083, filed Mar. 11, 2005, 16 pages.

U.S. Office Action mailed on Mar. 5, 2007, for U.S. Appl. No. 10/366,125, filed Feb. 12, 2003, 6 pages.

U.S. Office Action mailed on May 17, 2007, for U.S. Appl. No. 10/407,435, filed Apr. 4, 2003, 15 pages.

U.S. Office Action mailed on Oct. 5, 2007, for U.S. Appl. No. 11/094,387, filed Mar. 29, 2005, 22 pages.

Van Hinsbergh, V.W.M. et al. (1978). "Palmitate Oxidation by Rat Skeletal Muscle Mitochondria," *Archives of Biochemistry and Biophysics* 190(2):762-771.

Van Loan, Maria D. et al. (1999). "Monitoring Changes in Fat-Free Mass in HIV-Positive Men With Hypotestosteronemia and AIDS Wasting Syndrome Treated With Gonadal Hormone Replacement Therapy," *AIDS* 13:241-248.

Veenstra, Timothy D. et al. (2000). "Proteome Analysis Using Selective Incorporation of Isotopically Labeled Amino Acids," *J. Am. Soc. Mass. Spectrom.* 11:78-82.

Veerkamp, Jacques H. et al. (1986). "14CO2 Production Is No Adequate Measure of [14C]Fatty Acid Oxidation," *Biochemical Medicine and Metabolic Biology* 35:248-259.

Véniant, Murielle M. et al. (2000). "Defining the Atherogenicity of Large and Small Lipoproteins Containing Apolipoproteins B100," *J. Clin. Invest.* 106(12): 1501-1510.

Wadke, M. et al. (Jul. 1973). "Fatty Acid Synthesis by Liver Perfused with Deuterated and Tritiated Water," *Biochemistry* 12(14):2619-2624.

Wain-Hobson, S. (1995). "Virological Mayhem," *Nature* 373:102.

Waldeman, F.M. et al. (1991). "A Comparison Between Bromodeoxyuridine and 3 H Thymidine Labeling in Human Breast Tumors," *Modern Path.* 4(6):718-722.

Wang, Wei et al. (2000). "Effects of Nicotinic Acid on Fatty Acid Kinetics, Fuel Selection, and Pathways of Glucose Production in Women," *Am. J. Physiol. Endocrinol. Metab.* 279:E50-E59.

Waterlow, J.C. (1980). "Protein Turnover in the Whole Animal," *Invest. Cell Pathol.* 3:107-119.

Wei, X et al. (1995). "Viral Dynamics in Human Immunodeficiency Virus Type 1 Infection," *Nature* 373:117-122.

Winett, Richard et al. (2000). "Exercise Regimens for Men With HIV," *JAMA* 284(2):175-6.

Wolf, George (1995). "The Effect of Fasting and Fructose and Glucose Infusion on Gluconeogenesis and Triose Phosphate Flux in Rats in Vivo," *Nutrition Reviews* 53(10):299-302.

Wolfe, R. (1990). "Isotopic Measurement of Glucose and Lactate Kinetics," *Ann. Med.* 22:163-170.

Wolthers et al. (1998). "Rapid CD4+ T-Cell Turnover in HIV-1 Infection: a Paradigm Revisited," *Immunol. Today* 19(1):44-48.

Wolthers, K.C. et al. (1996). "T Cell Telomere Length in HIV-1 Infection: No Evidence for Increased CD4+ T Cell Turnover," *Science* 274:1543-1547.

Wood, H.G. et al. (1963). "Estimation of Pathways of Carbohydrate Metabolism," *Biochemische Zeitschrift* 338:809-847.

Zhang, Z-Q. et al. (Feb. 1998). "Kinetics of CD4+ T Cell Repopulation of Lymphoid Tissues after Treatment of HIV-1 Infection," *Proc. Nat!. Acad. Sci. USA* 95:1154-1159.

Zilversmit, D.B. et al. (1943). "On the Calculation of 'Turnover Time' and 'Turnover Rate' from Experiments Involving the Use of Labeling Agents," *J. of General Physiology* 26(3):325-331.

International Search Report and Written Opinion mailed Feb. 5, 2008, for PCT Application No. PCT/US2006/017167 filed May 3, 2006, 11 pages.

Jones, P. J. J. et al. (1990). "Evidence for Diurnal Periodicity in Human Cholesterol Synthesis," *Journal of Lipid Research* 31:667-673.

Mikkola, T. S. et al. (2003). "Serum Cholesterol Efflux Potential is an Independent Predictor of Coronary Artery Atherosclerosis," *Atherosclerosis* 170(1):31-38.

Mindham, M. A. et al. (1994). "Application of Simultaneous Spleen and Liver Perfusion to the Study of Reverse Cholesterol Transport," *Biochemical Journal* 302:207:213.

Naik, S. U. et al. (2006). "Pharmacological Activation of Liver X Receptors Promotes Reverse Cholesterol Transport In Vivo," *Circulation* 113:90-97.

U.S. Office Action mailed on Jan. 30, 2008, for U.S. Appl. No. 10/078,083, filed Mar. 11, 2005, 12 pages.

Di Buono, M. et al. (2000). "Comparison of Deuterium Incorporation and Mass Isotopomer Distribution Analysis for Measurement of Human Cholesterol Biosynthesis," *Journal of Lipid Research* 41:1516-1523.

Perochon, E. et al. (1997). "Radiolabeling of the Lipids of Chinese Hamster Ovary Cells with the Probe [3-(Trifluoromethyl)-3-(m-[$^{125}$I]iodophenyl)diazirine]," *Analytical Biochemistry* 254:109-118.

Rittenberg, D. et al. (Feb. 1937). "Deuterium as an Indicator in the Study of Intermediary Metabolism—VIII. Hydrogenation of Fatty Acids in the Animal Organism," *Journal of Biological Chemistry* 117:485-490.

Rittenberg, D. et al. (Sep. 1937). "Deuterium as an Indicator in the Study of Intermediary Metabolism—X. The Metabolism of Butyric and Caproic Acids," *Journal of Biological Chemistry* 120:503-510.

Schoenheimer, R. et al. (Mar. 1936). "Deuterium as an Indicator in the Study of Intermediary Metabolism—V. The Desaturation of Fatty Acids in Organism," *Journal of Biological Chemistry* 113:505-510.

Emken, Edward A. et al. (1983). "Incorporation of deuterium-labeled trans- and cis-13-octadeconoic acids in human plasma lipids," *Journal of Lipid Research* 24:34-41.

Gasparini, P. et al. (Mar. 1989). "Amplification of DNA from Epithelial Cells in Urine," *The New England Journal of Medicine* 320(12):809.

Patsalos, P. N. et al. (Oct. 1980). "Pattern of Myelin Breakdown During Sciatic Nerve Wallerian Degeneration: Reversal of the Order of Assembly," *The Journal of Cell Biology* 87:1-5.

Wolfe, R. et al. (1984). "Glucose Metabolism in Humans," *ACS Symposium Series* 258, Chapter 12, Turnund et al. ed., pp. 175-189.

Iyengar, V. et al. (1991). "Human Stools as a Source of Viable Colonic Epithelial Cells," *The FASEB Journal* 5:2856-2859.

Emken, E. A. (1994). "Metabolism of Dietary Stearic Acid Relative to Other Fatty Acids in Human Subjects," *The American Journal of Clinical Nutrition* 60(Suppl):1023S-1028S.

Hellerstein, M. K. (1996). "Synthesis of Fat in Response to Alterations in Diet: Insights from New Stable Isotope Methodologies," *Lipids* 31(Supp):S117-S125.

Wolthers, K. C. et al. (1996). "T Cell Telomere Length in HIV-1 Infection: No Evidence for Increased CD4+ T Cell Turnover," *Science* 274:1543-1547.

Gerling, B. et al. (1997). "Prediction of Liver Fibrosis According to Serum Collagen VI Level in Children with Cystic Fibrosis," *The New England Journal of Medicine* 336(22):1611-1612.

Rosin, M. P. et al. (Dec. 1, 1997). "The Use of Exfoliative Cell Samples to Map Clonal Genetic Alterations in the Oral Epithelium of High-Risk Patients," *Cancer Research* 57:5258-5260.

Nagasaka, S. et al. (May 1999). "Endogenous Glucose Production and Glucose Effectiveness in Type 2 Diabetic Subjects Derived From Stable-Labeled Minimal Modal Approach," *Diabetes* 48:1054-1056.

Collins, M. et al. (Mar. 15, 2000). "A Method for Measuring Mitochondrial Proliferation In Vivo Using 2H20 Incorporation Into Mitochondria DNA," FASEB Journal, 14(4):A620.

Sosa-Peinado, A. et al. (Jul. 2000). "Overexpression and Biosynthetic Deuterium Enrichment of TEM-1 Beta-Lactamase for Structural Characterization by Magnetic Resonance Methods," *Protein Expression and Purification* 19(2):235-245.

Ackermans, M. T. et al. (2001). "The Quantification of Gluconeogenesis in Healthy Men by $^2H_2O$ and [2-$^{13}$C]Glycerol Yields Different Results: Rates of Gluconeogenesis in Healthy Men Measured with $^2H_2O$ are Higher than those Measured with [2-$^{13}$C]Glycerol," *The Journal of Clinical Endocrinology & Metabolism* 86(5):2220-2226.

Boros, L. G. et al. (2001). "Genistein Inhibits Nonoxidative Ribose Synthesis in MIA Pancreatic Adenocarcinoma Cells: A New Mechanism of Controlling Tumor Growth," *Pancreas* 22(1):1-7.

Paku, S. (Apr. 2001). "Origin and Structural Evolution of the Early Proliferating Oval Cells in Rat Liver," *American Journal of Pathology* 158(4):1313-1323.

Sting et al. (2001). Breast Can Res and Treatment, 67:93-109.

Boros, L. G. et al. (Mar. 2002). "Metabolic Profiling of Cell Growth and Death in Cancer: Applications in Drug Discovery," *Drug Discovery Today* 7(6):364-372.

Oshima, M. et al. (2002). "COX Selectivity and Animal Models for Colon Cancer," *Current Pharmaceutical Design* 8:1021-1034.

Robosky, L. C. (2002). "In Vivo Toxicity Screening Programs Using Metabonomics," *Combinatorial Chemistry & High Throughput Screening* 5:651-662.

Propper, D. J. et al. (Jan. 2003). "Use of Positron Emission Tomography in Pharmacokinetic Studies to Investigate Therapeutic Advantage in a Phase I Study of 120-Hour Intravenous Infusion XR5000," *Journal of Clinical Oncology* 21(2)203-210.

Rittler, P. et al. (2003). "Effect of Tumor Removal on Mucosal Protein Synthesis in Patients with Colorectal Cancer," *American Journal of Physiology-Endocrinology and Metabolism* 284:E1018-E1021.

Clarke, R. B. (2005). "Isolation and Characterization of Human Mammary Stem Cells," *Cell Proliferation* 38:375-386.

International Search Report and Written Opinion mailed Aug. 8, 2006, for international application No. PCT/US05/10429, filed Mar. 29, 2005, 15 pages.

Restriction Requirement mailed on Apr. 4, 2006, for U.S. Appl. No. 10/519,121, 7 pages.

Sting et al. (Feb. 2006). *Nature* 439:993-997.

Supplementary Partial European Search Report mailed Jul. 25, 2006, for EP Application No. 02806603.3 filed Oct. 23, 2002, 5 pages.

Written Opinion mailed Jul. 14, 2006, by the Australian Patent Office for Singapore patent application No. 200502593-7, filed Nov. 4, 2003, 5 pages.

Zhang, B.-L. et al. (2006). "Deuterium NMR Study of the Origin of Hydrogen in Fatty Acids Produced in Vivo in Chicken," *European Journal of Lipid Science and Technology* 108:125-133.

Notice of Allowance and Fees Due mailed on May 3, 2007, for U.S. Appl. No. 10/519,121, filed Dec. 23, 2004, 7 pages.

U.S. Appl. No. 11/796,438, filed Apr. 26, 2007 for Hellerstein.

U.S. Office Action mailed on Dec. 14, 2007, for U.S. Appl. No. 10/701,990, filed Nov. 4, 2003, 8 pages.

"NCBI Blast: Protein Sequence (17 letters)," located at <http://blast.ncbi.nlm.nih.gov/Blast.cgi> visited on May 29, 2008, 5 pages.

Supplementary European Search Report mailed Sep. 19, 2008, for EP Application No. 05733311.4 filed Feb. 2, 2005, 9 pages.

Austrian Search Report and Written Opinion mailed Aug. 5, 2009, for SG Application No. 200717391-7 filed May 3, 2006, 7 pages.

Supplementary European Search Report mailed Jun. 30, 2009, for EP Application No. 05725448.4 filed Mar. 11, 2005, 7 pages.

Supplementary European Search Report mailed Jul. 28, 2009, for EP Application No. 04809469.2 filed Jun. 29, 2004, 4 pages.

Martin et al. (1998). "Discovery of a human liver glycogen phosphorylase inhibitor that lowers blood glucose in vivo," *Proc. Natl. Acad. Sci. USA* 95(4):1776-1781.

Backhouse, B. et al. (Mar. 1982). "Effects of haloperidol on cell proliferation in the early postnatal rat brain," *Neuropathology and Applied Neurobiology* 8(2):109-116.

Malberg, J. et al. (Dec. 15, 2000). "Chronic antidepressant treatment increases neurogenesis in adult rat hippocampus,"*J Neuroscience* 20(24):9104-9110.

Santarelli, L. et al. (Oct. 8, 2003). "Requirement of hippocampal neurogenesis for the behavioral effects of antidepressants," *Science* 301:805-809.

Wong, M-L et al. (Jan. 30, 2004). "From monoamines to genomic targets: a paradigm shift for drug discovery in depression," *Nature Reviews: Drug Discovery* 3(2):136-151.

Whittmann and Heinzle (2001). "Application of MALDI-TOF MS to lysine-producing Corynebacterium glutamicum: a novel approach for metabolic flux analysis," *Eur. J. Biochem.* 268:2441-2455.

Mcfarland et al., "Inhibition of DNA synthesis in neonatal rat brain regions caused by acute nicotine administration", Developmental Brain Research, vol. 58, No. 2, Feb. 22, 1991, pp. 223-229.

Ramakers et al., "Chronic suppression of bioelectric activity and cell survival in primary cultures of rat cerebral cortex: biochemical observations", European Journal of Neuroscience, vol. 3, No. 2, Feb. 1991, pp. 154-161.

Office Action received for Canadian Patent Application No. 2,498,378, mailed on Sep. 21, 2010, 3 pages.

European Search Report received for EP Patent Application No. 04812281.6, mailed on Oct. 6, 2010, 4 pages.

Hellerstein et al., "Subpopulations of long-lived and short lived T cells in advanced HIV-1 infection", The Journal of Clinical Investigation, vol. 112, No. 6, Sep. 2003, pp. 956-966.

Siler et al., "De novo lipogenesis, lipid kinetics, and whole-body lipid balances in humans after acute alcohol consumption1-3", The American Journal of Clinical Nutrition, vol. 70, 1999, pp. 928-936.

* cited by examiner

METHODS FOR MEASURING RATES OF REVERSE CHOLESTEROL TRANSPORT IN VIVO, AS AN INDEX OF ANTI-ATHEROGENESIS

CROSS-REFERENCE TO RELATED APPLICATION

This application is a Divisional application of U.S. application Ser. No. 10/519,121, filed Dec. 23, 2004, which claims priority to U.S. National Stage Application of International Application No. PCT/US03/29361, filed Sep. 15, 2003, which is an application claiming benefit of U.S. Provisional Application Ser. No. 60/410,352, filed Sep. 13, 2002, all of which are hereby incorporated by reference in their entirely.

FIELD OF THE INVENTION

The present invention relates to the field of cholesterol metabolism. In particular, methods for quantitatively measuring reverse cholesterol transport are described.

BACKGROUND OF THE INVENTION

Atherosclerosis, the most common form of arteriosclerosis, is a disease of large and medium-sized arteries (e.g., coronary, carotid, and lower extremity arteries), and of the elastic arteries, such as the aorta and iliac vessels. The atheroma, or fibrofatty plaque within the intima that consists of a lipid core and fibrous cap, is pathognomonic (*Robbins Pathologic Basis of Disease* 557 (Cotran et al. eds., 4th ed. 1989)). In addition to being a primary risk factor for myocardial and cerebral infarcts, atherosclerosis is responsible for such medical conditions as chronic lower extremity ischemia and gangrene, and for mesenteric occlusion. Despite a recent reduction in mortality from coronary heart disease, about 50% of all deaths in the United States are still attributed to atherosclerosis (*Scientific American Medicine §1* (Rubenstein et al. eds., 1991)).

Epidemiologic, postmortem, and angiographic studies have firmly established a causal relationship between elevated serum cholesterol levels and the genesis of atherosclerosis (Levine et al., *Cholesterol Reduction In Cardiovascular Disease*, N Eng J Med 332(8):512-521 (1995)). Although there is no single level of plasma cholesterol that identifies those at risk, in general, the higher the level, the higher the risk. However, the risk rises significantly with cholesterol levels above 200 mg/dl (*Robbins Pathologic Basis of Disease*, supra, at 559). Levels of total cholesterol are typically classified as being desirable (<200 mg/dl), borderline high (200-239 mg/dl), or high (≧240 mg/dl). Dietary treatment is usually recommended for patients with high risk levels of low density lipoprotein (LDL) cholesterol and for those with borderline-high risk levels who have at least 2 additional risk factors for atherosclerosis (e.g., hypertension, diabetes mellitus, cigarette smoking, etc.). However, dietary therapy has been found to be effective only in patients whose diets were higher than average in cholesterol and saturated fats (*Adult Treatment Panel II. National Cholesterol Education Program: Second Report of the Expert Panel on Detection, Evaluation, and Treatment of High Blood Cholesterol in Adults*, Circulation 89:1333-1445 (1994)), and would be ineffective in patients with a genetic predisposition to hypercholesterolemia. In the case of persistent high cholesterol levels, drug therapy may be prescribed.

Currently marketed drugs for the treatment of hypercholesterolemia work by such methods as inhibiting de novo cholesterol synthesis and/or stimulating clearance of LDL cholesterol by the LDL receptor (e.g., lovastatin), decreasing the production of very low density lipoprotein (VLDL) (e.g., gemfibrozil), or by inhibiting bile acid reabsorption in the intestines (e.g., cholestyramine). Examination of cholesterol metabolism, however, also reveals that the process of reverse cholesterol transport allows a pathway through which cholesterol may be removed from tissues and may exit the body. At present, there is no known method for measuring the rate of cholesterol flow through the reverse cholesterol transport pathway from tissue to excretion in a living organism.

Figure 1:
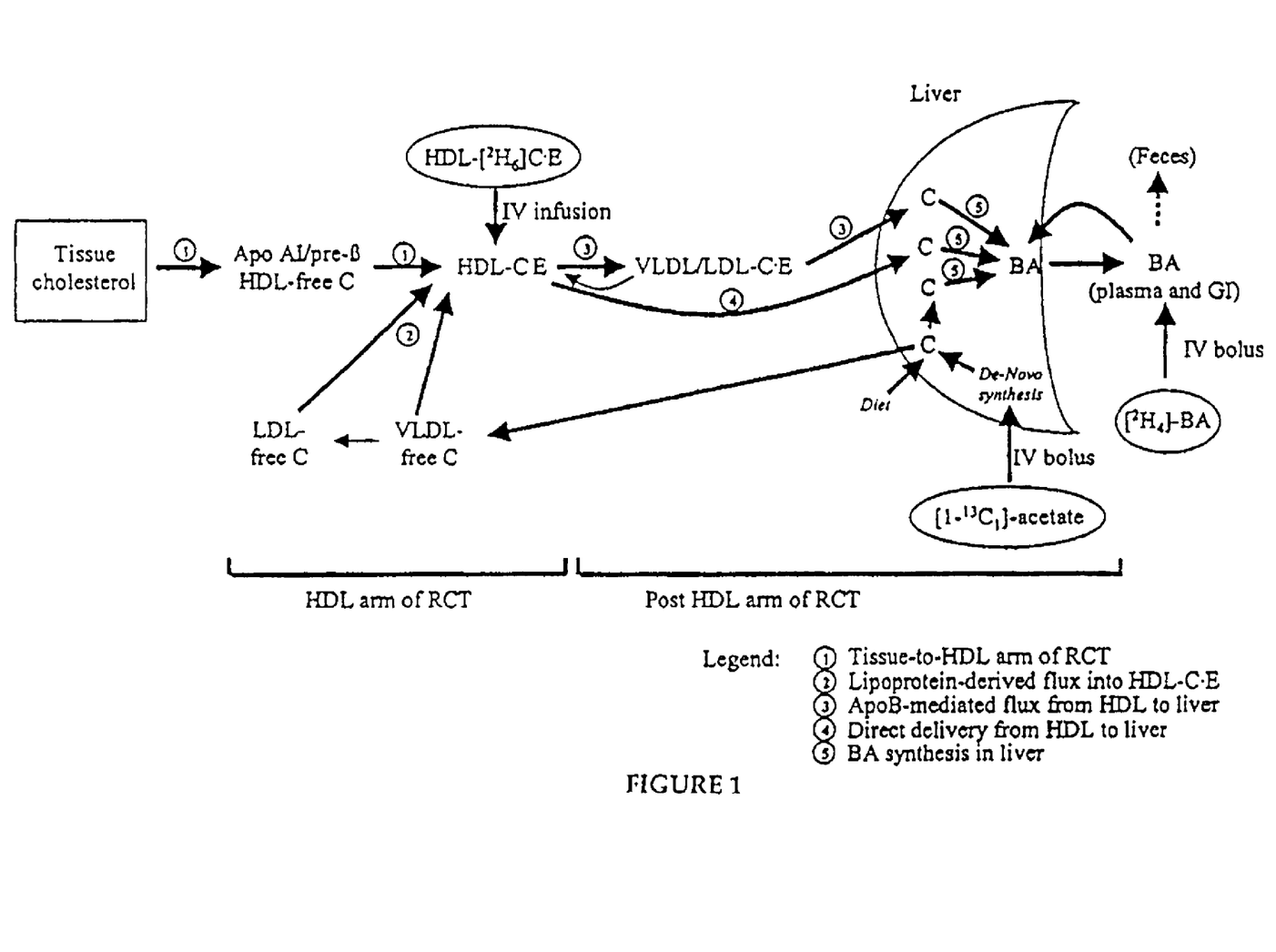
FIG. 1 illustrates the reverse cholesterol transport pathway.

Reverse cholesterol transport (RCT) is a biological pathway through which cholesterol is mobilized and transported from the peripheral tissues of the body to the liver. As shown in FIG. 1, there are two arms of the pathway, represented by efflux of cholesterol from extrahepatic tissues (the high density lipoprotein (HDL) arm or first arm of RCT) and transport of cholesterol from the bloodstream to the liver (post-HDL arm or second arm of RCT). Eventually, cholesterol is excreted into the bile, and then ultimately, from the body. RCT represents the only known biological pathway or active mechanism by which cholesterol can be removed from tissues. As mentioned above, because of the well-established role of cholesterol in atherogenesis, RCT is considered a key anti-atherogenic process and is generally believed to be the explanation for anti-atherogenic properties and clinical correlation with reduced cardiovascular risk of the high density lipoprotein (HDL) fraction of plasma.

However, HDL levels are now recognized to reflect only one component of the molecular pathway of RCT (FIG. 1), and do not necessarily reflect the true flow of cholesterol through the RCT pathway. The RCT pathway involves the transport of cholesterol from extrahepatic tissues into plasma by HDL, then delivery to IDL (intermediate density lipoprotein) via the action of lecithin-cholesterol acyl transferase (LCAT), and then eventually to LDL (low density lipoprotein). Thereafter, some of the LDL is taken up by the liver and excreted as bile acids into the intestines (Ganong W. F., *Review of Medical Physiology* 284-288 (15th ed. 1991)). Other pathways of RCT have been considered but the above-noted sequence is currently believed to most likely predominate.

The molecular details of the RCT pathway have come into increasing focus in the past several years. One important implication of these recent advances in molecular understanding is the recognition that plasma HDLc (HDL-cholesterol) levels in isolation may or may not reflect true flux through the pathway, depending upon the underlying mechanism responsible for the change in HDLc. For example, if the plasma concentration of HDLc in an individual represents flux from tissues through ABC(A)-1 (the ATP-binding cassette transporter) into plasma apoAI-containing particles, as in ABC(A)-I heterozygotes, then HDLc is a useful marker. However, if HDLc in another individual accumulates because of inhibition of delivery of HDLc to its acceptors (e.g., due to reduced cholesterol ester transfer protein activity, reduced hepatic SRBI (scavenger-receptor BI) activity), then HDLc levels will not reflect RCT. The situation can be particularly complex, when considering the impact on RCT of interventions that alter the production and fate of apoB containing particles, such as the statins. Because apoB particles are capable of carrying cholesterol forward (i.e., to the tissues) as well as in reverse (i.e., back to the liver), the actual fate of apoB particles in an individual may contribute to the efficiency of RCT at any plasma HDL level. The possibility of a dissociation between HDLc concentrations and RCT is thereby raised in the setting of effective statin therapy (or any other intervention that promotes return of VLDL and LDL particles to the liver).

Measuring the rate of a biochemical process such as RCT is more difficult than measuring the concentration of biochemical molecules. The former requires kinetic methods, while the latter involves static measurements. Kinetic measurements must include the dimension of time (i.e., a timed procedure must be performed), because all rates include time in the denominator (e.g., mg/min for biochemical rates, analogous to miles/hour for physical rates of motion). Typically, for biochemical kinetics, the molecule of interest or a precursor to it is labeled, and the flow of the label from the labeled molecule into various routes is measured over time.

Theoretically, tissue cholesterol may be labeled to follow its efflux from peripheral cells, but in practice, it has been essentially impossible to label non-hepatic cholesterol without labeling hepatic and blood cholesterol at the same time, whether the labeled material administered is cholesterol itself or its biosynthetic precursors (e.g., $^{14}C$-acetate, $^3H_2O$, or $^2H_2O$).

This is the case for several reasons: 1) hepatic cholesterol synthesis is very active, so that standard labeled biosynthetic precursors for cholesterol in the body will unavoidably label cholesterol in the liver; 2) there are no known labeled substrates that target peripheral (non-hepatic) tissues exclusively; 3) the cholesterol pools in peripheral tissues are very large and slow to turn over, so it takes a long time (weeks or months) to achieve adequate labeling; and 4) cholesterol exchanges rapidly between liver, blood and tissues, so that it quickly becomes impossible to distinguish the origin of labeled cholesterol and to infer directional rates of transfer.

For all these reasons, an in vivo method for measuring the rate of reverse cholesterol transport is needed and would have great utility for medical care and drug discovery and development.

SUMMARY OF THE INVENTION

To meet these needs, the present invention provides methods for determining the rate of reverse cholesterol transport. In one aspect, the first arm of reverse cholesterol transport may be determined in a living system. One or more isotopically labeled isotopically labeled high density lipoprotein (HDL) particles, isotopically labeled cholesterol molecules, or isotopically labeled cholesterol precursors are administered to the living system for a period of time sufficient for the label to be incorporated in plasma HDL. One or more isotopically labeled cholesterol molecules are obtained from plasma HDL. The isotopic content, isotopic pattern, rate of change of isotopic content, or isotopic pattern of the cholesterol molecules is then measured. The rate of dilution of the isolated labeled cholesterol molecules by endogenous unlabeled cholesterol is then calculated to determine the rate of the first arm of reverse cholesterol transport in the living system.

In another aspect, the rate of the second arm of reverse cholesterol transport may be determined. First, the rate of the first arm of reverse cholesterol transport is determined as described above. One or more isotopically labeled bile acids are administered to the living system in a manner different than the manner in which the label of the isotopically labeled HDL particle, isotopically labeled cholesterol, or isotopically labeled cholesterol precursor molecule. Alternatively, the isotopically labeled bile acids are labeled with a different isotope than the isotopically labeled HDL particle, isotopically labeled cholesterol, or isotopically labeled cholesterol precursor molecule. One or more isotopically labeled bile acids are obtained from the living system. The isotopic content, isotopic pattern, rate of change of isotopic content, or isotopic pattern of the bile acid is measured. The molecular flux rate of converting plasma HDL-cholesterol to bile acids is calculated to determine the rate of second arm of reverse cholesterol transport in the living system.

Suitable bile acids for labeling include, but are not limited to, cholic acid, chenodeoxycholic acid, deoxycholic acid, and lithocholic acid. Preferably, the bile acid is cholic acid.

Techniques for isotopically labeling molecules, e.g., cholesterol, bile acids, and the like, are well known in the art. The isotopes that may be used for labeling include, but are not limited to, $^2H$, $^3H$, $^{13}C$, $^{14}C$, or $^{18}O$. The preferred cholesterol molecules for labeling are cholesterol esters.

Instead of being reconstituted ex vivo, in another variation, the HDL particles may be formed in vivo, by administering isotopically labeled cholesterol or an isotopically labeled cholesterol precursor to the subject, followed by isolation and purification of the labeled HDL from plasma and re-introduction to a different subject or to the same subject.

Furthermore, the methods of the present invention may be applied to assess the effect of drug agents on the risk for atherosclerosis. In general, the method involves administering the drug agent to a subject, comparing the rate of reverse cholesterol transport in the subject before and after administration of the drug agents or in comparison to matched subject who have not received the drug agents, and calculating the difference in the rate of reverse cholesterol transport before and after administration of the drug agent. The drug agent may be a known pharmaceutical agent or a known deoxyribonucleic acid molecule that affects atherosclerosis.

In another variation, the effect of dietary modification on the risk for atherosclerosis is assessed by comparing the rate of reverse cholesterol transport in the subject before and after dietary modification, and calculating the difference in the rate of reverse cholesterol transport before and after dietary modification.

In yet a further variation, kits for determining the rate of reverse cholesterol transport are provided. The kits may include labeled HDL particles, labeled cholesterol, labeled bile acids, or a combination thereof, and instructions for use of the kit. The kit may optionally also include tools for administration of labeled HDL particles, labeled cholesterol precursors, or labeled bile acids to the subject and instruments for collecting a sample from the subject.

DETAILED DESCRIPTION OF THE INVENTION

The present invention provides a biochemical test for quantitatively measuring reverse cholesterol transport in vivo using isotopically labeled cholesterol and bile acids.
General Techniques Practice of the present invention will generally utilize, unless otherwise indicated, conventional techniques of molecular biology, microbiology, cell biology, biochemistry, and immunology, which are within the skill of the art. Such techniques are fully explained in the literature, for example, in Cell Biology: A Laboratory Notebook (J. E. Cellis, ed., 1998); Current Protocols in Molecular Biology (F. M. Ausubel et al., eds, 1987); Short Protocols in Molecular Biology (Wiley and Sons, 1999); *Mass Isotopomer Distribution Analysis: A Technique for Measuring Biosynthesis and Turnover of Polymers* (Hellerstein et al., Am J Physiol 263 (Endocrinol Metab 26):E988-E1001 (1992)); and Mass Isotopomer Distribution Analysis at Eight Years Theoretical, Analytic, and Experimental Considerations (Hellerstein et al., Am J Physiol 276 (Endocrinol Metab 39):E1146-1170 (1999)). Furthermore, procedures employing commercially available assay kits and reagents will typically be used according to manufacturer defined protocols unless otherwise noted.

Definitions

By "living system" is meant herein any living entity including a cell, cell line, tissue, organ, and organism. Examples of organisms include any animal, preferably a vertebrate, more preferably a mammal, most preferably a human. Examples of mammals include nonhuman primates, farm animals, pet animals, for example cats and dogs, and research animals, for example mice, rats, and humans.

"Isotope labeled substrate" includes any isotope-labeled precursor molecule that is able to be incorporated into a molecule of interest in a living system. Examples of isotope labeled substrates include, but are not limited to, $^{2}H_2O$, $^{3}H_2O$, $^{2}H$-glucose, H-labeled amino acids, H-labeled organic molecules, $^{13}C$-labeled organic molecules, $^{14}C$-labeled organic molecules, $^{13}CO_2$, $^{14}CO_2$, $^{15}N$-labeled organic molecules and $^{15}NH_3$.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers).

"Isotopic content" refers to the content of isotopes in a molecule or population of molecules relative to the content in the molecule or population of molecules naturally (i.e., prior to administration or contacting of isotope labeled precursor molecules). The term "isotope enrichment" is used interchangeably with isotopic content herein.

"Isotopic pattern" refers to the internal relationships of isotopic labels within a molecule or population of molecules, e.g., the relative proportions of molecular species with different isotopic content, the relative proportions of molecules with isotopic labels in different chemical loci within the molecular structure, or other aspects of the internal pattern rather than absolute content of isotopes in the molecule.

"Exact mass" refers to mass calculated by summing the exact masses of all the isotopes in the formula of a molecule (e.g., 32.04847 for $CH_3NHD$).

"Nominal mass" refers to the integer mass obtained by rounding the exact mass of a molecule.

"Mass isotopomer" refers to family of isotopic isomers that is grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^{1}H$, $^{16}O$, $^{14}N$, etc. Other mass isotopomers are distinguished by their mass differences from $M_0$ (M1, M2, etc.). For a given mass isotopomer, the location or position of isotopes within the molecule is not specified and may vary (i.e., "positional isotopomers" are not distinguished).

"Mass isotopomer envelope" refers to the set of mass isotopomers comprising the family associated with each molecule or ion fragment monitored.

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonymously with the term "mass isotopomer pattern."

"Monoisotopic mass" refers to the exact mass of the molecular species that contains all $^{1}H$, $^{12}C$, $^{14}N$, $^{16}O$, $^{32}S$, etc. For isotopologues composed of C, H, N, O, P, S, F, Cl, Br, and I, the isotopic composition of the isotopologue with the lowest mass is unique and unambiguous because the most abundant isotopes of these elements are also the lowest in mass. The monoisotopic mass is abbreviated as m0 and the masses of other mass isotopomers are identified by their mass differences from m0 (m1, m2, etc.).

"Isotopically perturbed" refers to the state of an element or molecule that results from the explicit incorporation of an element or molecule with a distribution of isotopes that differs from the distribution that is most commonly found in nature, whether a naturally less abundant isotope is present in excess (enriched) or in deficit (depleted).

"Precursor molecule" refers to the metabolic precursors used during polymeric synthesis of specific molecules. Examples of precursor molecules include acetyl CoA, ribonucleic acids, deoxyribonucleic acids, amino acids, glucose, and glycine.

"Labeled water" as used herein refers to water that contains isotopes. Examples of labeled water include $^{2}H_2O$, $^{3}H_2O$, and $H_2^{18}O$. As used herein, the term "isotopically labeled water" is used interchangeably with "labeled water."

"Molecular flux rates," refers to the rate of synthesis and/or breakdown of molecules within a cell, tissue, or organism. "Molecular flux rates" also refers to a molecule's input into or removal from a pool of molecules, and is therefore synonymous with the flow into and out of said pool of molecules.

"Drug agent," "pharmaceutical agent," and "pharmacological agent" are used interchangeably and refer to chemical entities or biological agents (e.g., gene sequences, poly or monoclonal antibodies, cytokines, hormones, etc.) with useful or potentially useful therapeutic actions on biological processes that have been used or approved for use or are being tested or considered for use as therapeutic agents in humans or animals. Drug agents include, but are not limited to, any chemical compound or composition disclosed in, for example, the 13th Edition of *The Merck Index* (a U.S. publication, Whitehouse Station, N.J., USA), incorporated herein by reference in its entirety. "Known drugs" refers to agents or chemical entities that have been approved for therapeutic use as drugs in human beings in the United States.

By "molecule of interest" is meant any molecule, including but not limited to, cholesterol, cholesterol derivatives, bile acids, bile acid derivatives, amino acids, carbohydrates, fatty acids, peptides, sugars, lipids, nucleic acids, polynucleotides, glycosaminoglycans, polypeptides, or proteins that are present within a metabolic pathway within a living system.

An "individual" is a vertebrate, preferably a mammal, more preferably a human. The term "subject" is used interchangeably with "individual" herein.

A "biological molecule" refers to any molecule or molecules synthesized in a tissue or individual. A biological may refer to a class of molecules, such as, but not limited to, the set of total cellular proteins, genomic DNA, mitochondrial DNA, messenger RNA, or ribosomal RNA. Alternatively, biological molecules may be specific molecules with specific structural features or sequences, such as specific proteins (for example, apolipoprotein) or specific polynucleotide sequences (for example, a polynucleotide encoding apolipoprotein).

As used herein, an individual "at risk" is an individual who is considered more likely to develop a disease state or a physiological state than an individual who is not at risk. An individual "at risk" may or may not have detectable symptoms indicative of the disease or physiological condition, and may or may not have displayed detectable disease prior to the treatment methods (e.g., therapeutic intervention) described herein. "At risk" denotes that an individual has one or more so-called risk factors. An individual having one or more of these risk factors has a higher probability of developing one or more disease(s) or physiological condition(s) than an individual without these risk factor(s). These risk factors can include, but are not limited to, history of family members developing one or more diseases, related conditions, or pathologies, history of previous disease, age, sex, race, diet, presence of precursor disease, genetic (i.e., hereditary) considerations, and environmental exposure.

"Purifying" refers to methods of removing one or more components of a mixture of other similar compounds. For example, "purifying a protein or peptide" refers to removing a protein or peptide from one or more proteins or peptides in a mixture of proteins or peptides.

"Isolating" refers to separating one compound from a mixture of compounds. For example, "isolating a protein or peptide" refers to separating one specific protein or peptide from all other proteins or peptides in a mixture of one or more proteins or peptides.

A "biological sample" encompasses any sample obtained from a tissue or individual. The definition encompasses blood and other liquid samples of biological origin, that are accessible from an individual through sampling by minimally invasive or non-invasive approaches (e.g., urine collection, blood drawing, needle aspiration, and other procedures involving minimal risk, discomfort or effort). Biological samples include samples that have been manipulated in any way after their procurement, such as by treatment with reagents, solubilization, or enrichment for certain components, such as proteins or polynucleotides. The term "biological sample" also encompasses a clinical sample such as serum, plasma, other biological fluid, or tissue samples, and also includes cells in culture, cell supernatants and cell lysates.

"Biological fluid" includes but is not limited to urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, or other biological fluid.

Methods For Measuring Reverse Cholesterol Transport

The present invention provides methods for determining reverse cholesterol transport (RCT) in vivo by measuring the flow of unlabeled cholesterol from tissues into the bloodstream and/or from plasma HDL to bile acids, instead of the flow of labeled cholesterol.

In one aspect, the invention is directed to determining the rate of the first arm of reverse cholesterol transport by administering one or more isotopically labeled isotopically labeled high density lipoprotein (HDL) particles, isotopically labeled cholesterol molecules, or isotopically labeled cholesterol precursors to a living system. In a second aspect, the present invention is directed to determining the rate of the second arm of reverse cholesterol transport by determining the rate of the first arm of RCT, and administering one or more isotopically labeled bile acids to determine the molecular flux rate of the conversion of plasma cholesterol to bile acid (second arm of RCT). The methods are generally carried out in mammalian subjects, preferably humans. Mammals include, but are not limited to, primates, farm animals, sport animals, pets such as cats and dogs, guinea pigs, rabbits, mice, and rats.

I. Determining the Rate of the First Arm of Reverse Cholesterol Transport in the Living System In one aspect, the rate of the first arm of reverse cholesterol transport may be determined in a living system. One or more isotopically labeled isotopically labeled high density lipoprotein (HDL) particles, isotopically labeled cholesterol molecules, or isotopically labeled cholesterol precursors are administered to the living system for a period of time sufficient for the label to be incorporated in plasma HDL. One or more isotopically labeled cholesterol molecules are obtained from plasma HDL. The isotopic content, isotopic pattern, rate of change of isotopic content, or isotopic pattern of the cholesterol molecules is then measured. The rate of dilution of the isolated labeled cholesterol molecules by endogenous unlabeled cholesterol is then calculated to determine the rate of the first arm of reverse cholesterol transport in the living system.

A. Administering Isotopically Labeled High Density Lipoprotein (HDL) Particles, Isotopically Labeled Cholesterol Molecules, or Isotopically Labeled Cholesterol Precursors Isotopically labeled high density lipoprotein (HDL) particles, isotopically labeled cholesterol molecules, or isotopically labeled cholesterol precursors can be administered to a living system by various methods including, but not limited to, orally, parenterally, subcutaneously, intravenously, and intraperitoneally.

Isotopically labeled HDL particles are typically formed ex vivo (outside of the subject) for example by incubating apolipoproteinAI with egg phosphatidylcholine, free $^2H_6$-cholesterol, and cholic acid in the ratio of 1:80:8:80. Other suitable ranges can be determined by trial and error using procedures well known to those of ordinary skill in the art without undue experimentation. In a preferred embodiment, a plasma fraction or purified enzyme containing lecithin-cholesterol-acyl-transferase activity as well as serum albumin to carry phosphatidylcholine is then added, followed by removal of the enzymes and cholic acid by such techniques as size exclusion chromatography and dialysis, respectively. In general, the reconstituted HDL particles will be formed by mixing. Other methods for forming cholesterol-labeled HDL particles ex vivo are well known by or can be readily determined by those skilled in the art.

The HDL particles may be labeled in vivo by administering isotopically labeled cholesterol or an isotopically labeled precursor of cholesterol to the subject, followed by obtaining the labeled HDL from plasma. The labeling of cholesterol and cholesterol precursors using isotopes may be carried out by methods well known in the art. Isotopes that may be used for in vitro or in vivo cholesterol labeling include, but are not limited to $^2H$, $^3H$, $^{13}C$, $^{14}C$, or $^{18}O$. Cholesterol molecules suitable for labeling include free cholesterol, cholesterol ethers, and cholesterol esters. In a preferred variation, cholesterol esters are labeled.

The isotopically labeled high density lipoprotein (HDL) particles, isotopically labeled cholesterol molecules, or isotopically labeled cholesterol precursors may be continuously or repeatedly administered. Administration can be achieved in various ways. Administration may be accomplished continuously or repeatedly. The isotopically labeled high density lipoprotein (HDL) particles, isotopically labeled cholesterol molecules, or isotopically labeled cholesterol precursors may also be administered discontinuously. For the discontinuous labeling method, administration is accomplished one or more times, and then administration is discontinued and wash-out of labeled administered particle or molecule from body precursor pools is allowed to occur.

The methods of this invention are typically carried out in mammalian subjects, preferably humans. Mammals include, but are not limited to, primates, farm animals, sport animals, mice, and rats.

The isotopically labeled HDL particles, isotopically labeled cholesterol, or isotopically labeled precursors are generally administered in a suitable carrier at a predetermined volume and isotope concentration (to yield a certain specific activity). Suitable carriers include saline solution, triglyceride emulsions and intralipids. Isotope concentration typically varies depending on the purpose, e.g., if being given as a bolus or as maintenance administration. The isotopically labeled HDL particles, isotopically labeled cholesterol, or isotopically labeled precursors are administered for a length of time sufficient to achieve steady-state levels in the HDL-cholesterolin plasma.

B. Obtaining Isotopically labeled cholesterol from Plasma HDL

After administration of the labeled HDL particles, cholesterol, or cholesterol precursor molecules, a biological sample is obtained. Isotopically labeled cholesterol from the HDL fraction of the biological sample is obtained, partially purified, or isolated by techniques well known in the art.

The frequency of biological sampling can vary depending on different factors. Such factors include, but are not limited to, the nature of the biological sample, ease and safety of sampling, biological rate constants and turnover kinetics of the cholesterol, and the half-life of a drug agent that is administered to a subject or individual.

The labeled cholesterol may also be purified partially purified, or optionally, isolated, by conventional purification methods including high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the isotopically labeled cholesterol may be hydrolyzed or otherwise degraded to form smaller molecules. Hydrolysis methods include any method known in the art, including, but not limited to, chemical hydrolysis (such as acid hydrolysis) and biochemical degradation. Hydrolysis or degradation may be conducted either before or after purification and/or isolation of the cholesterol. The cholesterol also may be partially purified, or optionally, isolated, by conventional purification methods including high performance liquid chromatography (HPLC), fast performance liquid chromatography (FPLC), gas chromatography, gel electrophoresis, and/or any other methods of separating chemical and/or biochemical compounds known to those skilled in the art.

The cholesterol may also be derivatized. For example, the cholesterol may be derivatized to its TMS derivative prior to detection.

Methods of obtaining, purifying, and isolating cholesterol molecules may be found, for example, in Cell Biology: A Laboratory Notebook (J. E. Cellis, ed., 1998); Current Protocols in Molecular Biology (F. M. Ausubel et al., eds, 1987); Short Protocols in Molecular Biology (Wiley and Sons, 1999), as well as other sources well known in the art.

C. Measuring the Isotopic Content, Isotopic Pattern, Rate of Change of Isotopic Content, or Isotopic Pattern of the Isotopically Labeled Cholesterol Molecules The isotopic content, isotopic pattern, rate of change of isotopic content, or isotopic pattern of the isotopically labeled cholesterol molecules is then determined. The isotopic content, isotopic pattern, rate of change of isotopic content, or isotopic pattern of the isotopically labeled cholesterol molecules may be determined by methods including, but not limited to, mass spectrometry, nuclear magnetic resonance (NMR) spectroscopy, liquid scintillation counting or other methods known in the field. The isotopic content, isotopic pattern, rate of change of isotopic content, or isotopic pattern of cholesterol may be measured directly, or may be analyzed after the cholesterol has been chemically or biochemically modified.

1. Mass Spectrometry

Isotopic enrichment in isotopically labeled cholesterol molecules can be determined by various methods such as mass spectrometry, including but not limited to gas chromatography-mass spectrometry (GC-MS), isotope-ratio mass spectrometry, GC-isotope ratio-combustion-MS, GC-isotope ratio-pyrrolysis-MS, liquid chromatography-MS, electrospray ionization-MS, matrix assisted laser desorption-time of flight-MS, Fourier-transform-ion-cyclotron-resonance-MS, and cycloidal-MS.

Mass spectrometers convert molecules into rapidly moving gaseous ions and separate them on the basis of their mass-to-charge ratios. The distributions of isotopes or isotopologues of ions, or ion fragments, may thus be used to measure the isotopic enrichment in a plurality of molecules.

Generally, mass spectrometers include an ionization means and a mass analyzer. A number of different types of mass analyzers are known in the art. These include, but are not limited to, magnetic sector analyzers, electrospray ionization, quadrupoles, ion traps, time of flight mass analyzers, and Fourier transform analyzers.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, two or more mass analyzers may be coupled (MS/MS) first to separate precursor ions, then to separate and measure gas phase fragment ions. These instruments generate an initial series of ionic fragments of a molecule, and then generate secondary fragments of the initial ions. The resulting overlapping sequences allows complete sequencing of the protein, by piecing together overlaying "pieces of the puzzle", based on a single mass spectrometric analysis within a few minutes (plus computer analysis time).

The MS/MS fragmentation patterns and exact molecular mass determinations generated by mass spectrometry provide unique information regarding the chemical composition of molecules. An unknown molecule can be identified in minutes, by a single mass spectrometric analytic run. The library of chemical fragmentation patterns that is now available provides the opportunity to identify components of complex mixtures with near certainty.

Different ionization methods are also known in the art. One key advance has been the development of techniques for ionization of large, non-volatile macromolecules. Techniques of this type have included electrospray ionization (ESI) and matrix assisted laser desorption/ionization (MALDI). These have allowed MS to be applied in combination with powerful sample separation introduction techniques, such as liquid chromatography and capillary zone electrophoresis.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS is used to measure mass isotopomer abundances of organic molecules, hydrogen-labeled isotope incorporation from isotope-labeled water is amplified 3 to 7-fold, depending on the number of hydrogen atoms incorporated into the organic molecule.

In general, in order to determine a baseline mass isotopomer frequency distribution for the cholesterol or cholesterol derivative, such a sample is taken before infusion of an isotopically labeled precursor. Such a measurement is one means of establishing in the cell, tissue or organism, the naturally occurring frequency of mass isotopomers of the molecule of interest. When a cell, tissue or organism is part of a population of subjects having similar environmental histories, a population isotopomer frequency distribution may be used for such a background measurement. Additionally, such a baseline isotopomer frequency distribution may be estimated, using known average natural abundances of isotopes. For example, in nature, the natural abundance of $^{13}C$ present in organic carbon is 1.11%. Methods of determining such isotopomer frequency distributions are discussed below. Typically, samples of the molecule of interest are taken prior to and following administration of an isotopically labeled molecule to the subject and analyzed for isotopomer frequency.

D. Calculating the Rate of Dilution of isotopically Labeled Cholesterol Molecules The isotopic content, isotopic pattern, rate of change of isotopic content, or isotopic pattern of the isotopically labeled cholesterol molecules after administration is compared to the isotopic content, isotopic pattern, rate of change of isotopic content, or isotopic pattern of the isotopically labeled cholesterol molecules of the HDL particles or cholesterol precursors prior to administration to calculate the dilution of labeled cholesterol by unlabeled cholesterol. Dilution equations are known in the art and are described, for example, by Hellerstein et al. (1992), supra. The rate of dilution is then used to determine the molecular flux rate of tissue cholesterol into HDL, which corresponds to the first arm of RCT.

The rate of dilution of plasma cholesterol may be determined directly by subtracting the rate of infusion of unlabeled cholesterol from the rate of infusion of labeled cholesterol.

$$DilutionRate = \frac{InfusionRate(labeledCholesterol)}{Enrichment(LabeledCholesterol)} - InfusionRate(UnLabeledCholesterol)$$

II. Determining the Molecular Flux Rate of the Second Arm of Reverse Cholesterol Transport in the Living System In another aspect, the present invention is directed to first determining the rate of the first arm of reverse cholesterol transport, and second determining the rate of the second arm of reverse cholesterol transport.

A. Determining the Rate of the First Arm of RCT

To determine the rate of the second arm of RCT, the rate of the first arm of RCT is determined as described above. The rate of the second arm of reverse cholesterol transport is also determined as described below.

B. Administering One or more Isotopically Labeled Bile Acids

One or more isotopically labeled bile acids are administered to the living system in a manner different than the manner in which the label of the isotopically labeled HDL particle, isotopically labeled cholesterol, or isotopically labeled cholesterol precursor molecule are administered. Alternatively, the isotopically labeled bile acids have a different isotope label than the isotopically labeled HDL particle, isotopically labeled cholesterol, or isotopically labeled cholesterol precursor. One or more isotopically labeled bile acids is obtained from the living system, and the isotopic content, isotopic pattern, rate of change of isotopic content, or isotopic pattern of the bile acid is measured. The molecular flux rate of converting plasma HDL-cholesterol to bile acids is calculated to determine the rate of second arm of reverse cholesterol transport in the living system, thereby determining the rate of reverse cholesterol transport in the living system.

Suitable isotopically labeled bile acids include cholic acid, chenodeoxycholic acid, deoxycholic acid, and lithocholic acid. The preferred labeled bile acids are cholic acid and chenodeoxycholic acid. Isotopes that may be used for labeling the bile acids include, but are not limited to, $^2H$, $^3H$, $^{13}C$, $^{14}C$, or $^{18}O$.

The bile acids that are administered are labeled with an different isotope label from the isotope label used to label the HDL, cholesterol, or cholesterol precursor. Alternatively, the bile acids are labeled with the same isotope as the HDL, cholesterol, or cholesterol precursor but the bile acids are labeled in a manner that is distinguishable from the manner used to label the cholesterol or cholesterol precursor (e.g. different times, pulse, stopping vs. continuous and other distinguishable features well known to those skilled in the art).

The isotopically labeled bile acids may be administered simultaneously with, or separately from, the isotopically labeled HDL particles, isotopically labeled cholesterol, or isotopically labeled cholesterol precursors. The isotopically labeled bile acids are administered in a suitable carrier at a predetermined volume and isotope concentration (to yield a certain specific activity). Suitable carriers include saline solution, triglyceride emulsions and intralipids. Isotope concentration typically varies depending on the purpose, e.g., if being given as a bolus or as maintenance administration. Like the labeled HDL particles, labeled cholesterol, or labeled cholesterol precursors, and isotopically labeled bile acids are administered for a duration of time sufficient to achieve steady-state levels in the molecules of interest.

The administration of labeled bile acids to subjects may be orally or by paritoneal routes, e.g., intravascular infusion or subcutaneous, intramuscular, or intraperitoneal injection.

The bile acid may be obtained, and the isotopic content, isotopic pattern, rate of change of isotopic content, or rate of change of isotopic pattern may be calculated, as described for cholesterol, above.

If a labeled bile acid is administered in conjunction with labeled HDL to the subject, labeled cholesterol is obtained from the bile acids in the biological sample by techniques well known in the art. As described herein, the isotopic label of the administered bile acid is distinguishable from that of the administered HDL.

D. Measuring the Isotopic Content, Isotopic Pattern, Rate of Change of Isotopic Content, or Isotopic Pattern of Isotopically Labeled Bile Acids Isotopic enrichment of the isolated bile acids is then determined from both the administered HDL particles and the administered bile acids, and compared to the isotopic content of the HDL particles and bile acids prior to administration. The contribution from HDL cholesterol to bile acids and the dilution (total flux) of bile acids to labeled cholesterol in bile by unlabeled cholesterol is calculated. In this manner, the rate of the second arm of RCT (HDLc to bile acids; FIG. 1) can be calculated.

1. Measuring Relative and Absolute Mass Isotopomer Abundances

Measured mass spectral peak heights, or alternatively, the areas under the peaks, may be expressed as ratios toward the parent (zero mass isotope) isotopomer. It is appreciated that any calculation means which provide relative and absolute values for the abundances of isotopomers in a sample may be used in describing such data, for the purposes of the present invention.

2. Calculating Labeled: Unlabeled Proportion of Molecules of Interest

The proportion of labeled and unlabeled molecules of interest is then calculated. The practitioner first determines measured excess molar ratios for isolated isotopomer species of a molecule. The practitioner then compares measured internal pattern of excess ratios to the theoretical patterns. Such theoretical patterns can be calculated using the binomial or multinomial distribution relationships as described in U.S. Pat. Nos. 5,338,686, 5,910,403, and 6,010,846, which are hereby incorporated by reference in their entirety. The calculations may include Mass Isotopomer Distribution Analysis (MIDA). Variations of Mass Isotopomer Distribution Analysis (MIDA) combinatorial algorithm are discussed in a number of different sources known to one skilled in the art. The method is further discussed by Hellerstein and Neese (1999), as well as Chinkes, et al. (1996), and Kelleher and Masterson (1992), and U.S. patent application Ser. No. 10/279,399, all of which are hereby incorporated by reference in their entirety.

In addition to the above-cited references, calculation software implementing the method is publicly available from Professor Marc Hellerstein, University of California, Berkeley.

The comparison of excess molar ratios to the theoretical patterns can be carried out using a table generated for a molecule of interest, or graphically, using determined relationships. From these comparisons, a value, such as the value p, is determined, which describes the probability of mass isotopic enrichment of a subunit in a precursor subunit pool. This enrichment is then used to determine a value, such as the value $A_x^*$, which describes the enrichment of newly synthesized molecules for each mass isotopomer, to reveal the isotopomer excess ratio which would be expected to be present, if all isotopomers were newly synthesized.

Fractional abundances are then calculated. Fractional abundances of individual isotopes (for elements) or mass isotopomers (for molecules) are the fraction of the total abundance represented by that particular isotope or mass isotopomer. This is distinguished from relative abundance, wherein the most abundant species is given the value 100 and all other species are normalized relative to 100 and expressed as percent relative abundance. For a mass isotopomer $M_x$, $$\text{Fractional abundance of } M_x = A_x = \frac{\text{Abundance } M_x}{\sum_{i=0}^{n} \text{Abundance } M_i},$$

where 0 to $n$ is the range of nominal masses relative to the lowest mass ($M_0$) mass isotopomer in which abundances occur.

Δ Fractional abundance (enrichment or depletion)=

$$(A_x)_e - (A_x)_b = \left(\frac{\text{Abundance } M_x}{\sum_{i=0}^{n} \text{Abundance } M_i}\right)_e - \left(\frac{\text{Abundance } M_x}{\sum_{i=0}^{n} \text{Abundance } M_i}\right)_b,$$

where subscript e refers to enriched and b refers to baseline or natural abundance.

In order to determine the fraction of the molecules that were actually newly synthesized during a period of precursor administration, the measured excess molar ratio ($EM_x$) is compared to the calculated enrichment value, $A_x^*$, which describes the enrichment of newly synthesized biopolymers for each mass isotopomer, to reveal the isotopomer excess ratio which would be expected to be present, if all isotopomers were newly synthesized.

E. Calculating the Molecular Flux Rate of Converting HDL Cholesterol to Bile Acid The method of determining rate of synthesis includes calculating the proportion of mass isotopically labeled subunit present in the molecular precursor pool, and using this proportion to calculate an expected frequency of a molecule of interest containing at least one mass isotopically labeled subunit. This expected frequency is then compared to the actual, experimentally determined isotopomer frequency of the molecule of interest. From these values, the proportion of the molecule of interest which is synthesized from added isotopically labeled precursors during a selected incorporation period can be determined. Thus, the rate of synthesis during such a time period is also determined.

A precursor-product relationship may then be applied to determine the percentage of labeled bile acid from the isotopically labeled HDL, isotopically labeled cholesterol, or isotopically labeled cholesterol precursor. For the continuous labeling method, the isotopic enrichment is compared to asymptotic (i.e., maximal possible) enrichment and kinetic parameters (e.g., synthesis rates) are calculated from precursor-product equations. The fractional synthesis rate ($k_s$) may be determined by applying the continuous labeling, precursor-product formula:

$k_s = [-\ln(1-f)]/t,$ where f=fractional synthesis=product enrichment/asymptotic precursor/enrichment and t=time of label administration of contacting in the system studied.

For the discontinuous labeling method, the rate of decline in isotope enrichment is calculated and the kinetic parameters of the molecules of interest are calculated from exponential decay equations. Breakdown rate constants ($k_d$) may be calculated based on an exponential or other kinetic decay curve:

$$k_d = [-\ln f]/t.$$

The dilution rate of isotopically labeled bile acid may be calculated by equations known in the art such as, for example, the following equation:

$$DilutionRate = \frac{InfusionRate(labeledBileAcid)}{Enrichment(LabeledBileAcid)} - InfusionRate(LabeledBileAcid).$$

The rate of the second arm of RCT may be calculated by multiplying the percent of bile acid from cholesterol with the dilution rate in the living system according to equations known in the art, such as, for example, the following equation:

$$RateofSecondArm = \% \text{ BilefromCholesterol} \otimes \text{RateofBileTurnover}.$$

Uses of Determining the Rate of Reverse Cholesterol Transport (RCT)

The methods of the present invention may be used for a variety of purposes. Primarily, the methods are used to determine the rates of the first and second arms RCT in a subject. In turn, the rates may be used to assess the effect of various factors on atherogenesis.

For example, in one variation, the methods may be used to assess the effect of a drug agent on atherosclerosis. After administering the drug agent to a subject, the rate of the first arm or the second arm RCT in the subject before and after administration of the drug agent will be compared. The subject may or may not have atherosclerosis. The effect of the candidate drug agent will be determined by the change (e.g., increase, decrease, or no difference) in the rate measured before and after administration of the drug agent. The drug agent may be a known pharmaceutical agent or deoxyribonucleic acid molecule that is capable of affecting the first and/or second arm of RCT.

In another variation, the methods may be used to assess the effect of dietary modification on atherosclerosis. Similar to that described above, the effect is determined by the change (e.g., increase, decrease, or no difference) in the rate of first and/or second arm of RCT determined before and after dietary modification.

In a further variation, the invention provides kits for performing the methods of the invention. The kits may be formed to include such components as labeled HDL particles, labeled cholesterol, labeled bile acids, or a combination thereof, in varying isotope concentrations and as premeasured volumes. Furthermore, the kit preferably will be packaged with instructions for use of the kit components and with instructions on how to calculate cholesterol dilutions.

Other kit components, such as tools for administration of the labeled HDL particles, labeled cholesterol, or labeled bile acids (e.g., measuring cup, needles, syringes, pipettes, IV tubing), may optionally be provided in the kit. Similarly, instruments for obtaining samples from the subject (e.g., specimen cups, needles, syringes) may also be optionally provided.

The following example is provided to show that the method of the invention may be used to determine reverse cholesterol transport. Those skilled in the art will recognize that while specific embodiments have been illustrated and described, they are not intended to limit the invention.

EXAMPLES

Example 1

Measurement of Reverse Cholesterol Transport in an Animal Model

Figure 2:
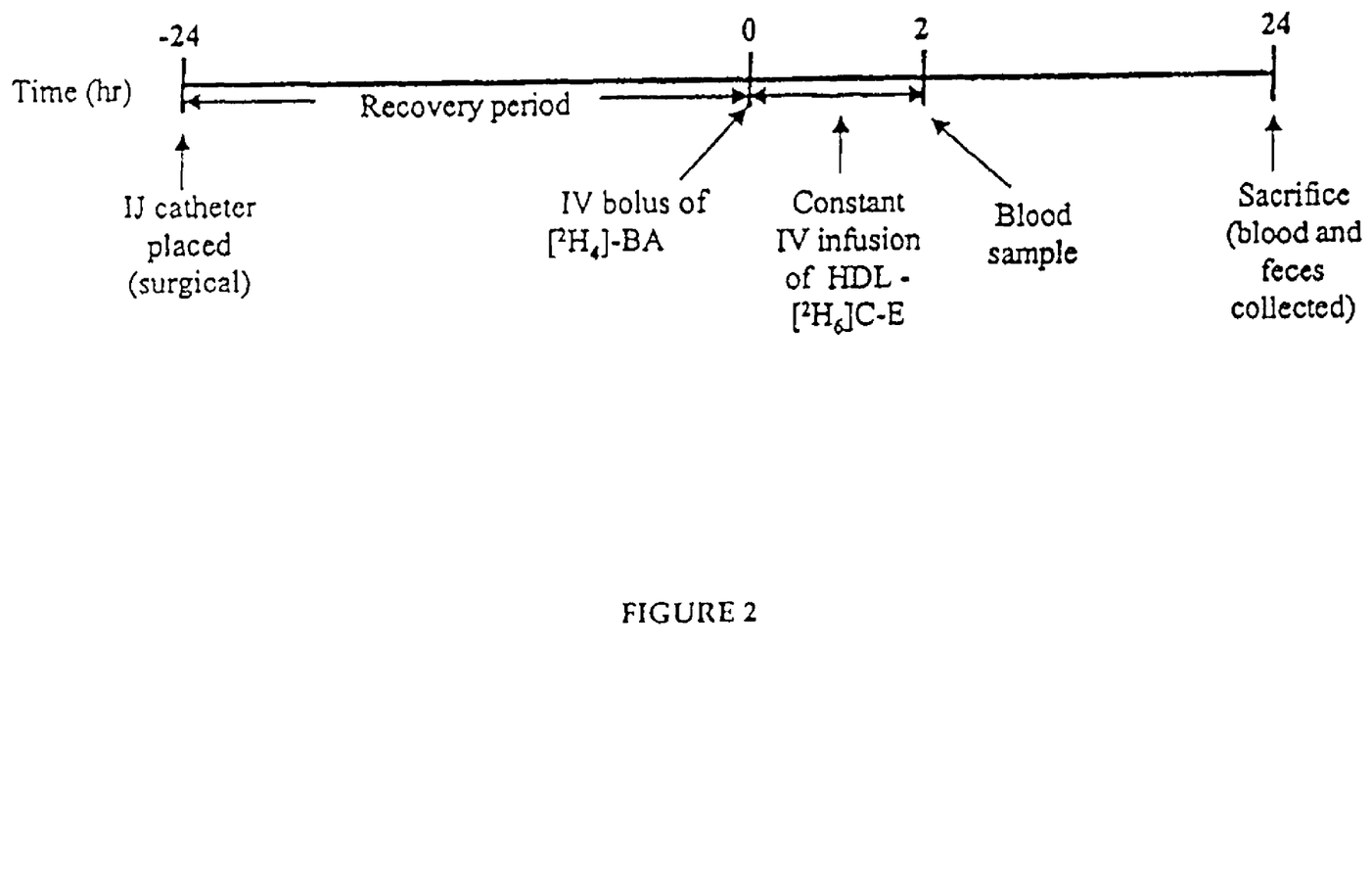
FIG. 2 is a timeline that demonstrates a protocol for determining the rate of reverse cholesterol transport.

FIG. 2 shows an experimental protocol that is used in an experiment involving an animal model, such as a rat model. Infusion catheters are surgically placed in the jugular vein of rats which are then allowed to recover for 24 hours. An IV bolus of [$^2H_4$]-BA and [1-$^{13}C_1$]-acetate is given followed by constant IV infusion of HDL-[$^2H_6$]C-E (cholesterol ester). Blood samples are obtained after 2 hours and at sacrifice 24 hours later. At sacrifice, feces are also collected.

Cholesterol from blood and fecal samples is then obtained. In each sample, the cholesterol is then derivatized to its TMS derivative and measured by mass spectrometry. The rate of the first arm of reverse cholesterol synthesis is calculated.

Example 2

Measuring Reverse Cholesterol Transport in a Murine Model

FIG. 2 shows an experimental protocol that is used in an experiment involving an animal model, such as a rat model. Infusion catheters are surgically placed in the jugular vein of rats which are then allowed to recover for 24 hours. An IV bolus of [$^2H_4$]-BA and [1-$^{13}C_1$]-acetate is given followed by constant IV infusion of HDL-[$^2H_6$]C-E (cholesterol ester). Blood samples are obtained after 2 hours and at sacrifice 24 hours later. At sacrifice, feces are also collected.

Cholesterol from blood and fecal samples is then obtained. In each sample, the cholesterol is then derivatized to its TMS derivative and measured by mass spectrometry. The bile acid is also obtained, derivatized, and measured by mass spectrometry. The rate of the first arm of reverse cholesterol transport is calculated based on the cholesterol measurement. The rate of the second arm of reverse cholesterol is calculated based on the bile acid measurement.

Applicants have not abandoned or dedicated to the public any unclaimed subject matter.

I claim:

1. A method of assessing an effect of a drug agent on atherosclerosis in a living system, the method comprising
    a) administering one or more isotopically labeled cholesterol molecules, isotopically labeled cholesterol molecules in high density lipoprotein (HDL) particles, or isotopically labeled cholesterol precursors to the living system;
    b) obtaining one or more isotopically labeled cholesterol molecules from plasma or plasma HDL in the living system;
    c) measuring an isotopic content, isotopic pattern, rate of change of isotopic content, or rate of change of isotopic pattern of the isotopically labeled cholesterol molecules;

d) calculating a rate of dilution by endogenous unlabeled cholesterol of the administered isotopically labeled cholesterol molecules, isotopically labeled cholesterol molecules in high density lipoprotein (HDL) particles, or isotopically labeled cholesterol precursors to determine a rate of a first arm of reverse cholesterol transport in the living system;

e) administering said drug agent to said living system; and f) determining a rate of a first arm of reverse cholesterol transport in the living system according to steps a) through d) after said administering step e), wherein a difference in the rate of the first arm of reverse cholesterol transport before and after administration of said drug agent to the living system identifies the effect of the drug agent on atherosclerosis.

2. The method of claim 1, wherein the drug agent is a known pharmaceutical agent.

3. The method of claim 1, wherein the drug agent is a deoxyribonucleotide molecule.

4. A method of assessing an effect of dietary modification on atherosclerosis in a living system, said method comprising:

a) administering one or more isotopically labeled cholesterol molecules, isotopically labeled cholesterol molecules in high density lipoprotein (HDL) particles, or isotopically labeled cholesterol precursors to the living system;

b) obtaining one or more isotopically labeled cholesterol molecules from plasma or plasma HDL in the living system;

c) measuring an isotopic content, isotopic pattern, rate of change of isotopic content, or rate of change of isotopic pattern of the isotopically labeled cholesterol molecules;

d) calculating a rate of dilution by endogenous unlabeled cholesterol of the administered isotopically labeled cholesterol molecules, isotopically labeled cholesterol molecules in high density lipoprotein (HDL) particles, or isotopically labeled cholesterol precursors to determine a rate of a first arm of reverse cholesterol transport in the living system;

e) subjecting said living system to the dietary modification; and f) determining a rate of a first arm of reverse cholesterol transport in the living system according to steps a) through d) after said subjecting step e), wherein a difference in the rate of the first arm of reverse cholesterol transport before and after subjecting said living system to the dietary modification identifies the effect of dietary modification on atherosclerosis in said living system.

* * * * *